(12) United States Patent
Pikulenko et al.

(10) Patent No.: US 11,439,830 B2
(45) Date of Patent: Sep. 13, 2022

(54) T-WAVE MORPHOLOGY ANALYSIS FOR PATHOLOGICAL EVENT DETECTION

(71) Applicant: Medtronic, Inc., Minneapolis, MN (US)

(72) Inventors: Inna A. Pikulenko, St. Paul, MN (US); Gary L. Berg, Edina, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 25 days.

(21) Appl. No.: 16/825,291

(22) Filed: Mar. 20, 2020

(65) Prior Publication Data

US 2020/0298002 A1 Sep. 24, 2020

Related U.S. Application Data

(60) Provisional application No. 62/821,756, filed on Mar. 21, 2019.

(51) Int. Cl.
*A61B 5/35* (2021.01)
*A61N 1/362* (2006.01)
*A61B 5/00* (2006.01)
*A61N 1/365* (2006.01)
*A61B 5/283* (2021.01)
*A61B 5/363* (2021.01)
*A61B 5/366* (2021.01)

(52) U.S. Cl.
CPC ............ *A61N 1/3621* (2013.01); *A61B 5/283* (2021.01); *A61B 5/35* (2021.01); *A61B 5/363* (2021.01); *A61B 5/366* (2021.01); *A61B 5/74* (2013.01); *A61N 1/3655* (2013.01); *A61N 1/36521* (2013.01); *A61N 1/36535* (2013.01); *A61N 1/36557* (2013.01); *A61N 1/36585* (2013.01); *A61N 1/36592* (2013.01)

(58) Field of Classification Search
CPC .. A61N 1/35; A61N 1/355; A61B 1/35; A61B 1/355
See application file for complete search history.

(56) References Cited

U.S. PATENT DOCUMENTS 4,336,810 A 6/1982 Anderson et al.
5,507,782 A 4/1996 Kieval et al.
5,792,065 A 8/1998 Xue et al.
(Continued)

OTHER PUBLICATIONS

Rugg et al., "Epilepsy and the Heart", The British Journal of Cardiology, vol. 17, Issue 5, Sep./Oct. 2010, 7 pages.
(Continued)

*Primary Examiner* — George R Evanisko

(57) ABSTRACT

A medical device senses cardiac electrical signals including T-waves attendant to ventricular myocardial repolarizations and detects a T-wave template condition associated with non-pathological changes in T-wave morphology. The device generates a T-wave template from T-waves sensed by the sensing circuit during the T-wave template condition. After generating the T-wave template, the device acquires a T-wave signal from the cardiac electrical signal and compares the acquired T-wave signal to the T-wave template. The device detects a pathological event in response to the acquired T-wave signal not matching the T-wave template.

27 Claims, 9 Drawing Sheets

(56) References Cited

U.S. PATENT DOCUMENTS

| | | |
|---|---|---|
| 6,412,490 B1 | 7/2002 | Lee |
| 6,650,931 B1 | 11/2003 | McClure et al. |
| 7,024,243 B1 | 4/2006 | Bornzin et al. |
| 7,027,858 B2 | 4/2006 | Cao et al. |
| 7,155,282 B1 | 12/2006 | Min et al. |
| 7,769,436 B1* | 8/2010 | Boileau .................. A61B 5/349 600/509 |
| 8,019,410 B1* | 9/2011 | Bharmi .................. A61B 5/366 600/516 |
| 8,195,291 B2 | 6/2012 | Norton et al. |
| 8,532,785 B1 | 9/2013 | Crutchfield et al. |
| 9,744,364 B2 | 8/2017 | Gordon et al. |
| 10,045,710 B2 | 8/2018 | Higgins et al. |
| 2006/0224075 A1 | 10/2006 | Gunderson et al. |
| 2007/0038138 A1* | 2/2007 | Gill ....................... A61N 1/3702 600/513 |
| 2007/0156056 A1 | 7/2007 | Min et al. |
| 2008/0082014 A1 | 4/2008 | Cao et al. |
| 2008/0161870 A1 | 7/2008 | Gunderson |
| 2008/0208069 A1* | 8/2008 | John ........................ A61B 5/35 600/509 |
| 2009/0018595 A1 | 1/2009 | Bharmi et al. |
| 2009/0270747 A1* | 10/2009 | van Dam .............. A61B 5/1116 600/509 |
| 2016/0256063 A1* | 9/2016 | Friedman ........... A61B 5/02455 |
| 2018/0028828 A1 | 2/2018 | Cao et al. |

OTHER PUBLICATIONS

Strzelczyk et al., "Postictal Increase in T-Wave Alternans After Generalized Tonic-Clonic Seizures", Epilepsia, vol. 52, Issue 11, 6 pages.

Nei et al., "EKG Abnormalities During Partial Seizures in Refractory Epilepsy", Epilepsia, vol. 41, Issue 5, 7 pages.

Rosenbaum, "T-Wave Alternans in the Sudden Cardiac Death in Heart Failure Trial Population Signal or Noise?", American Heart Association, 2008, 4 pages.

Hosaka et al., "Correlation Between Surface and Intracardiac Electrocardiogram in a Patient with Inappropriate Defibrillation Shocks Due to Hyperkalemia", Internal Medicine, vol. 48, 2009, 4 pages.

Koul et al., "Hyperkalemia Induced T Wave Oversensing Leading to Loss of Biventricular Pacing and Inappropriate ICD Shocks", Pace, vol. 27, May 2004, 4 pages.

Alizadeh et al., "Inappropriate ICD Discharge Due to T-Wave Oversensing in a Patient with the Brugada Syndrome", Journal of Interventional Cardiac Electrophysiology, vol. 15, 2006, 4 pages.

Cohen et al., "An Unusual Resolution of T-Wave Oversensing in an Implantable Cardioverter Defibrillator in a Child with Long QT Syndrome", Journal of Interventional Cardiac Electrophysiology, vol. 25, 2009, 4 pages.

Srivathsan et al., "T-Wave Oversensing and Inappropriate Shocks: A Case Report", Published on behalf of the European Society of Cardiology, doi: 10.1093/eurospace/eun083, 2008, 4 pages.

PCT Search Report dated Jul. 7, 2020, corresponding to counterpart PCT Application No. PCT/US2020/023523; 4 pages.

* cited by examiner

500

| 502 AS-VS T-Wave Templates | | | 504 AP-VS T-Wave Templates | | |
|---|---|---|---|---|---|
|  520a |  520b |  520c |  |  |  |
| Status byte = x | Status byte = x | Status byte = x | Status byte = x | Status byte = x | Status byte = x |
| 65-85 | 85-105 | 105-125 | 65-85 | 85-105 | 105-125 |
| 510 | 512 | 514 | 510 | 512 | 514 |

530 points to the Status byte label in the AS-VS section.

| 506 AS-VP T-Wave Templates | | | 508 AP-VP T-Wave Templates | | |
|---|---|---|---|---|---|
|  |  |  |  |  | |
| Status byte = x | Status byte = x | Status byte = x | Status byte = x | Status byte = x | Status byte = x |
| 65-85 | 85-105 | 105-125 | 65-85 | 85-105 | 105-125 |
| 510 | 512 | 514 | 510 | 512 | 514 |

800

| T-WAVE ATTRIBUTE | MONITOR | DETECTION CRITERIA | MONITORING TIME | TEMPLATE CONDITIONS |
|---|---|---|---|---|
| AMPLITUDE | YES/NO | %CHANGE | | |
| SLEW RATE | YES/NO | %CHANGE | | |
| AREA | YES/NO | %CHANGE | | |
| WIDTH | YES/NO | %CHANGE | | |
| SYMMETRY | YES/NO | %CHANGE | | |
| ST SEGMENT | YES/NO | %CHANGE | | |
| QT INTERVAL | YES/NO | %CHANGE | | |
| INVERSION | YES/NO | YES/NO | | |

FIG. 9

T-WAVE MORPHOLOGY ANALYSIS FOR PATHOLOGICAL EVENT DETECTION

CROSS REFERENCE TO RELATED APPLICATIONS

This application claims the benefit of the filing date of provisional U.S. Patent Application No. 62/821,756, filed Mar. 21, 2019, the content of which is incorporated herein by reference in its entirety.

TECHNICAL FIELD

The disclosure relates generally to medical devices and, in particular, to a medical device and method for analyzing T-wave morphology for predicting a pathological event.

BACKGROUND

A variety of medical devices for monitoring a physiological condition of a patient and/or delivering a therapy are available or have been proposed. These medical devices may be external medical devices, such as bedside devices or wearable devices, or implantable medical devices (IMDs). Some medical devices may employ one or more elongated electrical leads carrying stimulation electrodes, sense electrodes, and/or other sensors. Medical devices may deliver therapy to or monitor conditions of a variety of organs, nerves, muscle or tissue, such as the heart, brain, stomach, spinal cord, pelvic floor, or the like. Implantable medical leads may be configured to position electrodes or other sensors at desired locations for delivery of electrical stimulation or sensing of physiological signals. For example, electrodes or sensors may be carried along a distal portion of a lead that is extended subcutaneously, transvenously, or submuscularly. A proximal portion of the lead may be coupled to an IMD housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to sense intrinsic cardiac electrical signals for monitoring the heart rhythm and deliver electrical stimulation pulses to the heart to address abnormal cardiac rhythms.

Other examples of IMDs include neurostimulators and muscle stimulators which may deliver electrical stimulation pulses to the neuromuscular system or brain using intramuscular electrodes or nerve cuff electrodes carried by medical leads. Still other IMDs may be in the form of a drug pump for delivering a pharmacological agent intramuscularly or transvenously via a catheter, or a mechanical circulatory support device, such as a ventricular assist device, to enhance cardiac hemodynamic function. These various therapy delivery IMDs may generally be used to treat an abnormal condition or alleviate pain or symptoms associated with disease.

SUMMARY

In general, the disclosure is directed to techniques for monitoring T-wave morphology by a medical device for detecting or predicting a pathological event. T-waves attendant to the repolarization of the ventricular myocardium may be altered during or preceding a pathological event, which may or may not be a cardiac event. A medical device operating according to the techniques disclosed herein senses cardiac electrical signals including T-waves and generates T-wave templates for multiple, different T-wave template conditions. Each T-wave template condition is a condition that is associated with non-pathological changes in T-wave morphology that are not indicative of the pathological event being monitored for. T-wave morphology monitoring for detecting the pathological event is performed by sensing a T-wave, determining a current T-wave template condition present at the time of sensing the T-wave, and comparing the sensed T-wave to the T-wave template previously stored for that T-wave template condition. The pathological event is detected or predicted based on the comparative analysis when the sensed T-wave is different than the stored T-wave template.

In one example, the disclosure provides a medical device including a sensing circuit configured to sense a cardiac electrical signal comprising T-waves attendant to ventricular myocardial repolarizations and a control circuit. The control circuit is configured to detect a T-wave template condition associated with non-pathological changes in T-wave morphology and generate a T-wave template from at least one T-wave sensed by the sensing circuit during the detected T-wave template condition. After generating the T-wave template, the control circuit acquires a T-wave signal from the cardiac electrical signal sensed by the sensing circuit, compares the acquired T-wave signal to the T-wave template, determines that the T-wave signal does not match the T-wave template, and detects a pathological event in response to at least the T-wave signal not matching the T-wave template. The control circuit is further configured to generate a notification of the detected pathological event.

In another example, the disclosure provides a method including sensing a cardiac electrical signal comprising T-waves attendant to ventricular myocardial repolarizations and detecting a T-wave template condition associated with non-pathological changes in T-wave morphology. The method further includes generating a T-wave template from at least one T-wave sensed during the detected T-wave template condition. After generating the T-wave template, the method includes acquiring a T-wave signal from the sensed cardiac electrical signal, comparing the T-wave signal to the T-wave template, determining that the T-wave signal does not match the T-wave template and detecting a pathological event in response to determining that at least the T-wave signal does not match the T-wave template. The method further includes generating a notification of the detected pathological event.

In another example, the disclosure provides a non-transitory, computer-readable storage medium comprising a set of instructions which, when executed by a medical device, cause the medical device to sense a cardiac electrical signal comprising T-waves attendant to ventricular myocardial repolarizations, detect a T-wave template condition associated with non-pathological changes in T-wave morphology, and generate a T-wave template from at least one T-wave sensed from the cardiac electrical signal during the detected T-wave template condition. After generating the T-wave template, the instructions cause the medical device to acquire a T-wave signal from the sensed cardiac electrical signal, compare the acquired T-wave signal to the T-wave template, determine that the T-wave signal does not match the T-wave template, and detect a pathological event in response to the T-wave signal not matching the T-wave template. The instructions further cause the medical device to generate a notification of the detected pathological event.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 9 is a conceptual diagram of a T-wave monitoring programming window that may be generated and displayed by an external programming device.

DETAILED DESCRIPTION

Figure 1:
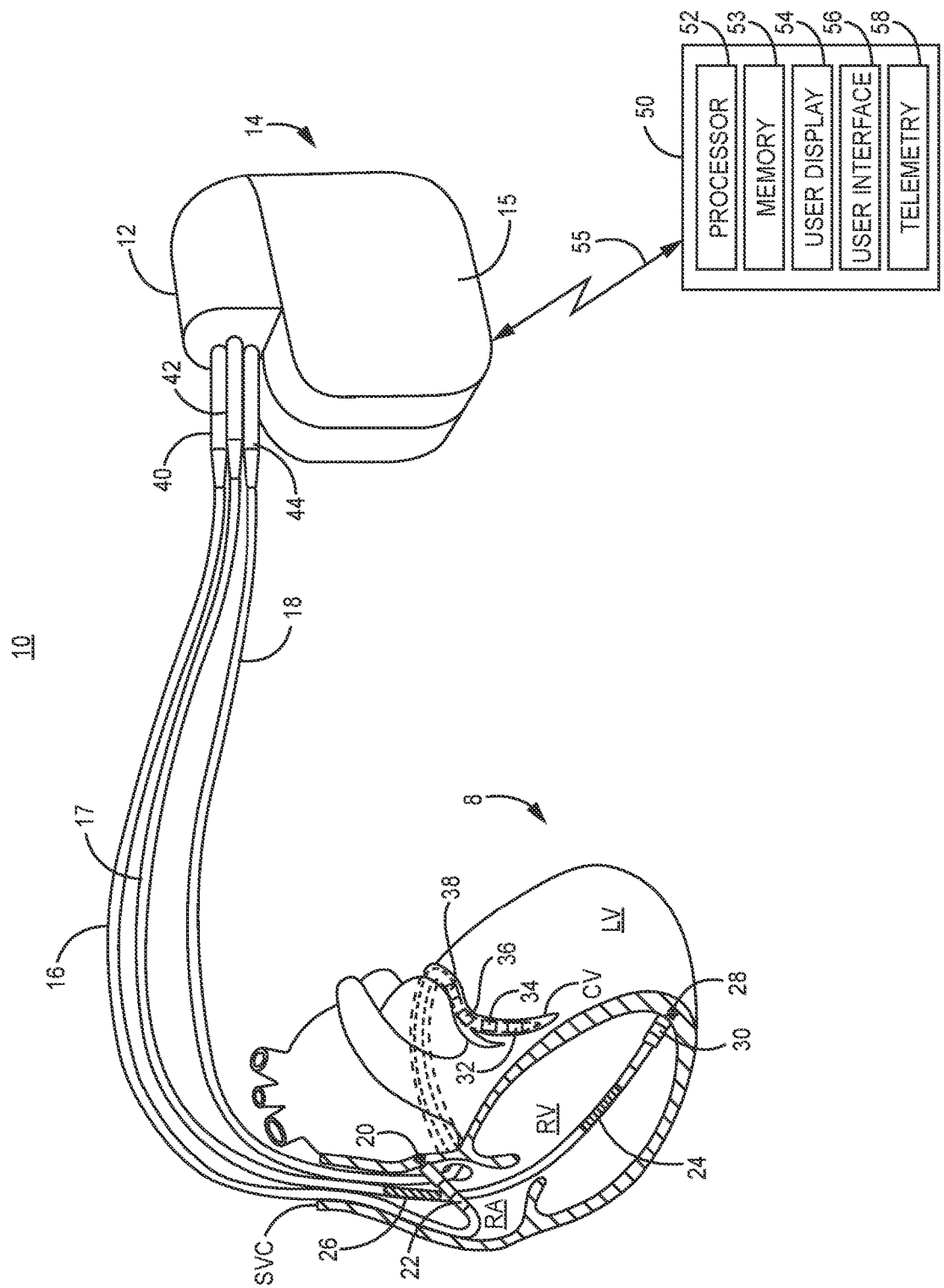
FIG. 1 is a conceptual diagram of one example of a medical device system 10 configured to perform T-wave morphology analysis for detecting or predicting a pathological event according to one example.

In general, this disclosure describes a medical device configured to perform techniques for monitoring T-waves for detecting or predicting a pathological event. The term "T-wave morphology" as used herein refers to aspects of the T-wave signal that may include the overall shape of the T-wave signal waveform as well as specific features of the T-wave signal and timing aspects of the T-wave signal, e.g., the time of the T-wave signal or a specific feature thereof relative to other cardiac signal features such as the Q-wave, R-wave, and S-wave. The T-wave morphology may be altered during or preceding a pathological event, such as myocardial infarction, cardiac arrhythmias such as non-sinus ventricular tachycardia (VT) or ventricular fibrillation (VF), an epileptic seizure, renal failure, hyperkalemia, hypokalemia, hyperglycemia, and hypoglycemia, insulin shock, and medication dosing complications such as medication non-compliance, underdose or overdose as examples. However, T-wave morphology may also be altered during non-pathological changes in a patient condition. Such patient conditions may include heart rate, changes between a paced cardiac rhythm and a non-paced cardiac rhythm, changes in patient posture or changes in patient physical activity, as examples. The techniques disclosed herein provide a medical device and method for analyzing T-wave morphology for detecting or predicting a pathological event based on a change in T-wave morphology, even in the presence of T-wave morphology changes that may occur with changes in one or more patient conditions, which may not be associated with the pathological event that is being detected or predicted.

As used herein, "non-pathological" with reference to a patient condition that is used as a T-wave template condition refers to a condition that is either non-pathological (e.g., sinus heart rate, patient physical activity level, or patient body posture) or is at least not the pathological event that is being detected or predicted. For example, in a patient that experiences a chronic or intermittent condition that is considered abnormal, that condition may alter the T-wave in a way that is considered "normal" for that patient when the pathological event being monitored for is not present. An example of this is a patient that experiences chronic or intermittent atrial tachyarrhythmia, such as atrial fibrillation or atrial flutter. The atrial rhythm condition, which may change between a normal sinus rhythm and an atrial tachyarrhythmia, may be considered to be a "non-pathological" T-wave template condition for the purposes of monitoring T-waves as described herein for detecting a pathological event that is not the atrial tachyarrhythmia. For the patient that experiences intermittent atrial tachyarrhythmias, a T-wave altered during the atrial tachyarrhythmia compared to normal sinus rhythm may be a "normal" T-wave morphology for that patient when the pathological event is not occurring or imminent. The condition of atrial rhythm (e.g., normal sinus or atrial tachyarrhythmia) may be a condition that results in T-wave changes that are not predictive or correlated to a pathological event that is being monitored for, such as epileptic seizure, renal failure, insulin shock, etc.

In some cases, the "non-pathological" condition is a condition that may be abnormal but is considered relatively benign or is being treated or corrected by an implantable medical device and is not the pathological event that is being detected or predicted. In another example, QRS changes may occur with changes in intrinsic ventricular conduction that are being addressed or treated by a pacemaker to promote a normal cardiac rhythm and promote electrical and mechanical synchrony. T-wave morphology, as well as QRS morphology, may change depending on the state of the ventricular conduction system (e.g., bundle branch block or AV conduction block) and state of pacing (e.g., ventricular sensing or ventricular pacing). Such changes in T-wave morphology may represent the "normal" T-wave morphologies for the given patient when the pathological event being monitored for is not present or imminent. As such, even though a ventricular conduction abnormality may generally be considered a pathological condition, for the purposes of the T-wave monitoring techniques disclosed herein, a change in ventricular condition, QRS morphology or state of ventricular paced rhythm may be considered a non-pathological condition for the purposes of generating T-wave templates that are considered "normal" for the given patient when a different pathological event being monitored for is not present or imminent.

The techniques disclosed herein may be implemented in a variety of implantable or external, e.g., wearable, medical devices which may be monitoring-only devices without therapy delivery capabilities or a device capable of both monitoring and delivering therapy. As examples, with no limitation intended, the techniques disclosed herein may be implemented in an implantable or external cardiac monitor, an implantable or external cardiac pacemaker or defibrillator, an implantable or external neurostimulator, a deep brain stimulator, heart assist device, or a drug pump. In some examples, the medical device performing the techniques disclosed herein for detecting or predicting a pathological event may be capable of delivering a therapy that is not necessarily for treatment or alleviation of the pathological event being detected through analysis of T-wave morphology. For example, the T-wave morphology analysis techniques disclosed herein may be implemented in a neurostimulator or cardiac pacemaker configured to deliver therapeutic neurostimulation or cardiac electrical stimulation pulses, yet the T-wave morphology analysis may be performed to predict a pathological event such as insulin shock or epileptic seizure that is not directly treated by the therapeutic electrical stimulation pulses. The pathological event being detected based on a change in T-wave morphology may be a cardiac-related pathological event, such as a cardiac conduction block or non-sinus tachyarrhythmia, or a non-cardiac related pathological event, such as epileptic seizure, insulin shock, etc.

In some cases the T-wave morphology change may be predictive of a pathological event that has not yet occurred but may be imminent. As used herein, "detection" of a pathological event may refer to detecting a pathological event this is occurring or detecting a pathological event that is expected to occur but may not yet be occurring, i.e., is predicted to occur.

FIG. 1 is a conceptual diagram of one example of a medical device system 10 configured to perform T-wave morphology analysis for detecting or predicting a pathological event according to one example. System 10 includes IMD 14 coupled to transvenous leads 16, 17 and 18 for sensing cardiac electrical signals and delivering cardiac electrical stimulation therapy in each of the right atrium (RA), right ventricle (RV) and left ventricle (LV) of heart 8. In this example, IMD 14 may be configured as a multi-chamber pacemaker and defibrillator capable of delivering cardiac resynchronization therapy (CRT). CRT includes delivering pacing pulses in the LV, RV and/or RA for improving mechanical synchrony of the right and left ventricles with each other and/or with the atria, and thereby promotes more efficient pumping of the heart 8. Accordingly, IMD 14 is coupled to three leads 16, 17 and 18 in this example to provide multi-chamber sensing and pacing. IMD 14 may additionally be capable of delivering high voltage cardioversion or defibrillation (CV/DF) shocks for treating cardiac tachyarrhythmias.

In other examples, however, the techniques disclosed herein may be implemented in a single chamber, dual chamber or multi-chamber cardiac pacemaker, with or without CV/DF capabilities. Furthermore, it is to be understood that any IMD capable of sensing a cardiac electrical signal that includes T-wave signals attendant to ventricular myocardial depolarizations may be adapted to perform the techniques disclosed herein. The multi-chamber cardiac sensing and cardiac pacing therapy capabilities described in conjunction with IMD 14 are not required for practicing the presently disclosed techniques for monitoring T-wave morphology and detecting pathological events. IMD 14 is illustrative of one type of medical device that may be configured for performing T-wave monitoring for detecting pathological events.

Figure 3:
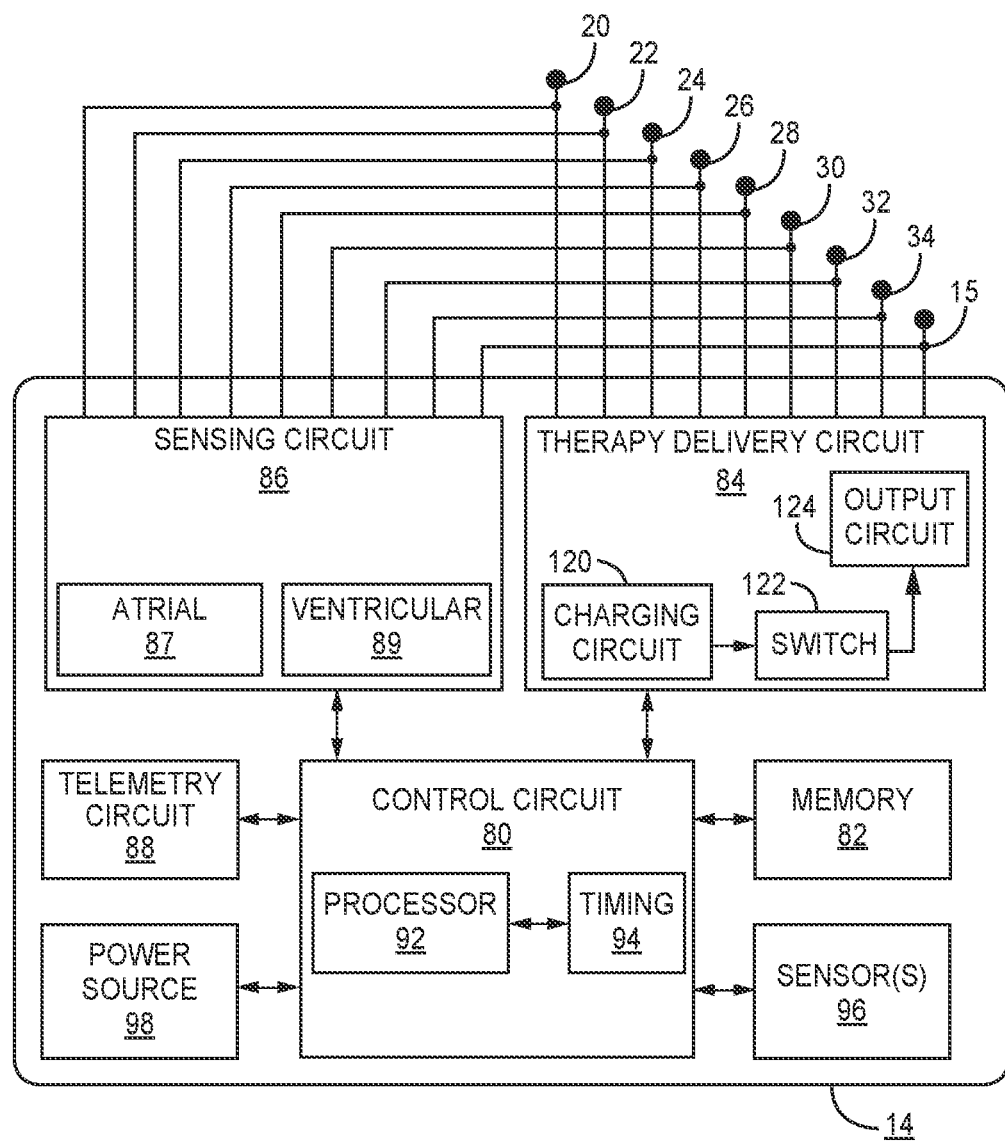
FIG. 3 is a conceptual diagram of an example configuration of a medical device that is configured to detect T-wave morphology changes for detecting or predicting a pathological event.

IMD 14 includes a connector assembly 12 coupled to a housing 15 that encloses circuitry configured to perform IMD functions, such as a processor, cardiac electrical signal sensing circuitry and therapy delivery circuitry as further described in conjunction with FIG. 3. Connector assembly 12, sometimes referred to as a "header," is hermetically sealed to housing 15 and includes, in this example, three connector bores for receiving a proximal lead connector 40, 42 and 44 of each of the respective leads 16, 17 and 18 to provide electrical communication between electrodes carried by the distal portion of each lead and the sensing and therapy delivery circuitry enclosed by housing 15. Housing 15 is formed from a biocompatible material, such as a stainless steel or titanium alloy. In some examples, the housing 15 may include an insulating coating over at least outer portions of housing 15. Examples of insulating coatings include parylene, urethane, PEEK, or polyimide among others. Housing 15 may be hermetically sealed to enclose IMD circuitry and protect IMD circuitry from blood and body fluids.

Leads coupled to IMD 14 may include RA lead 16, RV lead 17 and a coronary sinus (CS) lead 18. RA lead 16 may carry a distal tip electrode 20 and ring electrode 22 spaced proximally from tip electrode 20 for sensing atrial electrical signals, e.g., P-waves, and delivering RA pacing pulses. RA lead 16 may be positioned such that its distal end is in the vicinity of the RA and the superior vena cava and includes insulated electrical conductors extending through the elongated lead body from each of electrodes 20 and 22 to the proximal lead connector 40.

RV lead 17 includes pacing and sensing electrodes 28 and 30 shown as a tip electrode 28 and a ring electrode 30 spaced proximally from tip electrode 28. The electrodes 28 and 30 provide sensing and pacing in the RV and are each connected to a respective insulated conductor within the body of RV lead 17. Each insulated conductor is coupled at its proximal end to proximal lead connector 42. RV lead 17 is positioned such that its distal end is in the RV for sensing RV electrical signals, such as R-waves attendant to ventricular depolarizations, and delivering pacing pulses in the RV. In some examples, IMD 14 is capable of delivering high voltage pulses for cardioverting or defibrillating heart 8 in response to detecting a tachyarrhythmia. In this case, RV lead 17 may include defibrillation electrodes 24 and 26, which may be elongated coil electrodes used to deliver high voltage CV/DF therapy, also referred to a "shocks" or "shock pulses."

Defibrillation electrode 24 may be referred to as the "RV defibrillation electrode" or "RV coil electrode" because it is carried along the body of RV lead 17 such that it is positioned substantially within the RV when distal pacing and sensing electrodes 28 and 30 are positioned for pacing and sensing in the RV. For example, Tip electrode 28 may be positioned at an endocardial location of the RV apex. Defibrillation electrode 26 may be referred to as a "superior vena cava (SVC) defibrillation electrode" or "SVC coil electrode" because it is carried along the body of RV lead 17 such that it is positioned at least partially along the SVC when the distal end of RV lead 17 is advanced within the RV. The IMD housing 15 may serve as a subcutaneous defibrillation electrode in combination with one or both of RV coil electrode 24 and SVC coil electrode 26 for delivering CV/DF shocks to heart 8. While electrodes 24 and 26 are referred to herein as defibrillation electrodes, it is to be understood that electrodes 24 and 26 may be used for sensing cardiac electrical signals, delivering cardiac pacing pulses or delivering anti-tachycardia pacing (ATP) therapy and are not necessarily limited to only being used for delivering high voltage CV/DV shock pulses. In some examples, electrodes 24 and 26 may be used in sensing T-wave signals for generating T-wave templates and for monitoring for change in T-wave morphology indicative of a pathological event. Each of electrodes 24, 26, 28 and 30 are connected to a respective insulated conductor extending within the body of lead 17. The proximal end of the insulated conductors are coupled to corresponding connectors carried by proximal lead connector 42, e.g., a DF-4 connector, at the proximal end of lead 17 for providing electrical connection to IMD 14.

CS lead 18 may be advanced within the vasculature of the left side of the heart via the coronary sinus and a cardiac vein (CV). CS lead 18 is shown as a quadripolar lead having four electrodes 32, 34, 36 and 38 that may be selected in various bipolar or unipolar electrode vectors for sensing cardiac electrical signals from the LV and delivering cardiac pacing pulses to the LV, e.g., during CRT delivery. In other examples, CS lead 18 may include one or more electrodes for sensing cardiac electrical signals and delivering pacing pulses to the LV. The electrodes 32, 34, 36 and 38 are each coupled to respective insulated conductors within the body of CS lead 18, which provides electrical and mechanical connection to the proximal lead connector 44, coupled to IMD connector assembly 12.

The various pacing and sensing electrodes 20, 22, 28, 30, 32, 34, 36 and 38 may be selected in bipolar combinations for sensing and pacing in the respective RA, RV or LV. In some examples, housing 15 may be used as an electrode, sometimes referred to as a "can" electrode, for selection in a unipolar pacing or sensing electrode vector with any of electrodes 20, 22, 28, 30, 32, 34, 36 or 38. A unipolar or bipolar sensing electrode vector may be selected for acquiring T-wave signals for establishing T-wave templates and detecting changes in T-wave morphology. A unipolar sensing electrode vector may be selected from among the ventricular electrodes 28, 30, 32, 34, 36 and 38 carried by RV lead 17 and CS lead 18 paired with housing 15, RV coil electrode 24 or SVC coil electrode 26. A bipolar sensing electrode vector for acquiring T-wave signals may be selected from electrodes 28, 30, 32, 34, 36 and 38 carried by RV lead 17 and CS lead 18 and used for sensing cardiac electrical signals including T-waves.

It is recognized that numerous sensing and electrical stimulation electrode vectors may be available using the various electrodes carried by one or more of leads 16, 17 and 18. Alternate lead systems may be substituted for the three lead system illustrated in FIG. 1. For example, a medical device performing the T-wave morphology monitoring techniques disclosed herein may be coupled to one or more transvenous leads, such as leads 16, 17 and 18 and/or one or more extra-cardiac leads that extend subcutaneously, submuscularly or substernally. Examples of other IMDs, such as an extra-cardiovascular IMD system, in which the T-wave morphology analysis techniques disclosed herein may be implemented are generally disclosed in U.S. Pat. No. 10,045,710 (Higgins, et al.), incorporated herein by reference in its entirety.

An external device 50 is shown in wireless telemetric communication with IMD 14 via a communication link 55. Communication link 55 may be established using a radio frequency (RF) link such as BLUETOOTH®, Wi-Fi, Medical Implant Communication Service (MICS) or other communication bandwidth. External device 50 may be referred to as a "programmer" used by a physician, technician, nurse, clinician or other qualified user for programming operating parameters in IMD 14. External device 50 may be located in a clinic, hospital or other medical facility. External device 50 may alternatively be embodied as a home monitor or a handheld device that may be used in the patient's home or another location to allow a patient or other user to interact with IMD 14 or remote monitoring of the patient and IMD 14 operations. External device 50 may correspond to the MYCARELINK™ Patient Monitor available from Medtronic, Inc. Minneapolis Minn., USA, in one example.

IMD operating parameters, such as sensing and therapy delivery control parameters, may be programmed into IMD 14 using external device 50. External device 50 includes an external processor 52, memory 53, user display 54, user interface 56 and telemetry unit 58. External processor 52 controls external device operations and processes data and signals received from IMD 14. External processor 52 provides user display 54 with therapy delivery data, cardiac electrical signal data including T-wave morphology data, pathological events detected or predicted based on T-wave morphology analysis, cardiac arrhythmia episode data, and/or other device- or patient-related data retrieved from IMD 14 for generating a display of the data for observation and review by a clinician.

The user display 54 generates a display of data received from IMD 14 and may include a graphical user interface that facilitates programming of one or more sensing parameters, arrhythmia detection parameters, therapy delivery parameters and the like by a user interacting with external device 50. External device 50 may display other data and information relating to IMD functions to a user for reviewing IMD operation and programmed parameters as well as cardiac electrical signals or other physiological data that is retrieved from IMD 14 during an interrogation session. User interface 56 may include a mouse, touch screen, or other pointing device, keyboard and/or keypad to enable a user to interact with external device 50 to initiate a telemetry session with IMD 14 for retrieving data from and/or transmitting data to IMD 14 and for selecting and programming desired sensing and therapy delivery control parameters, tachyarrhythmia detection algorithms and other operating parameters into IMD 14. According to the techniques disclosed herein, various control parameters for sensing T-waves, acquiring T-wave signal segments, determining T-wave templates, determining T-wave template conditions, determining T-wave signal features for comparison to a T-wave template and criteria for detecting or predicting a pathological event based on a comparative analysis between one or more T-wave signals and a T-wave template may be programmed using external device 50.

External telemetry unit 58 includes a transceiver and antenna configured for bidirectional communication with an implantable transceiver and antenna included in IMD 14. In some examples, external device 50 may include a programming head that is placed proximate IMD 14 to establish and maintain a communication link 55, and in other examples external device 50 and IMD 14 may be configured to communicate using a distance telemetry algorithm and circuitry that does not require the use of a programming head and does not require user intervention to maintain a communication link 55. It is contemplated that external device 50 may be in wired or wireless connection to a communications network via telemetry unit 58 for transferring data to a centralized database or computer to allow remote management of the patient. Remote patient management systems may be configured to utilize the presently disclosed techniques to enable a clinician to review T-wave signal data including templates and results of comparative analyses and detected pathological event information received from IMD 14. A centralized computer or database may receive a warning or notification of a pathological event detected by IMD 14 via telemetry unit 58.

As discussed above, IMD 14 is one illustrative example of an IMD that may perform T-wave morphology analysis for detecting a pathological event. Other cardiac devices which may include T-wave monitoring include single chamber and dual chamber pacemakers or implantable cardioverter defibrillators, which may be coupled to transvenous or extra-cardiovascular leads or be leadless devices wholly implantable within the heart. The techniques disclosed herein are not limited to cardiac device capable of cardiac electrical stimulation therapies. Furthermore, the techniques disclosed herein may be implemented in an external device, which may be a wearable device, such as a cardiac signal monitor implemented in a housing of a watch or carried by a band, belt, vest or other wearable substrate carrying cardiac electrical signal sensing electrodes in contact with the patient's skin.

Figure 2:
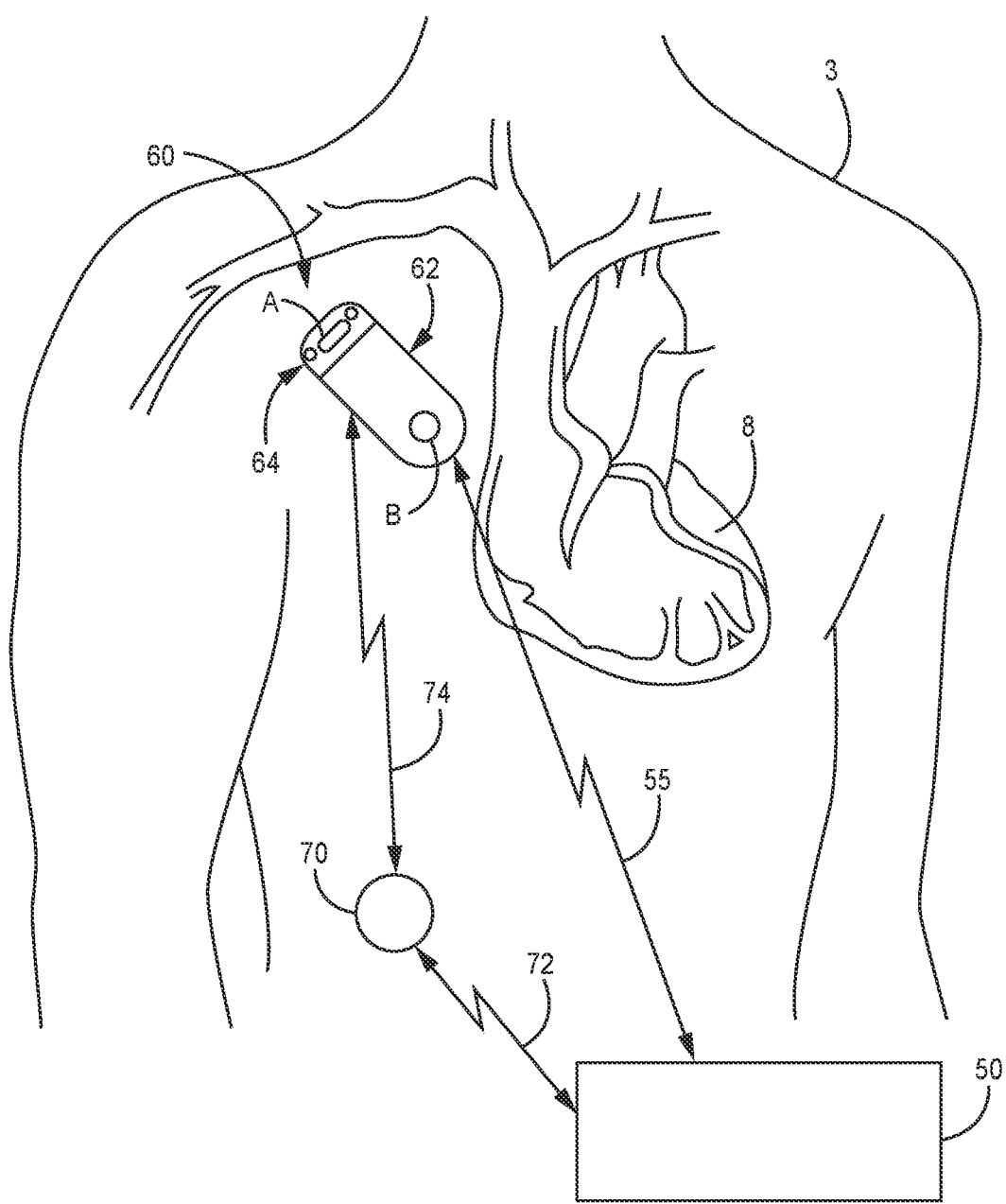
FIG. 2 is a conceptual diagram of an IMD system configured to sense cardiac electrical signals for detecting T-wave signal changes for predicting or detecting a pathological event according to another example.

FIG. 2 is a conceptual diagram of an IMD 60 configured to sense cardiac electrical signals for detecting T-wave signal changes for predicting or detecting a pathological event according to another example. IMD 60 may be a cardiac monitor having cardiac electrical signal sensing capabilities without having therapy delivery capabilities. In other examples, IMD 60 may be neurostimulator having electrodes for sensing cardiac electrical signals including T-waves and for delivering therapeutic electrical stimulation pulses. IMD 60 is shown implanted subcutaneously in the upper thoracic region of a patient's body 3. IMD 60 may be implanted at a location that enables cardiac electrical signal sensing with adequate T-wave signal strength for detecting changes in T-wave amplitude. IMD 60 may be implanted subcutaneously, submuscularly or substernally in an anterior, lateral or posterior location and may be aligned with heart 8 or superior or inferior to heart 8. In some examples, IMD 60 is positioned over the fourth intercostal space on the left hemi-thorax at an approximate forty-five degree angle or parallel to the sternal border to promote high quality T-wave signal and amplitude. The final position of IMD 60 may be selected through testing of multiple orientations and/or locations to identify an implant orientation and location resulting in maximized T-wave amplitude and/or otherwise obtain a preferred T-wave waveform shape, e.g., a monophasic waveform vs. a biphasic or multi-phasic waveform.

When IMD 60 includes neurostimulation capabilities, IMD 60 may be implanted at other anatomical locations as needed to deliver therapeutic electrical stimulation pulses to a target nerve or tissue site and sense cardiac electrical signals including T-waves and may be coupled to medical electrical leads extending away from IMD 60 for positioning electrodes at therapy delivery site and/or positioning electrodes outside the heart, e.g., subcutaneously or submuscularly, for sensing cardiac electrical signals for T-wave morphology monitoring. For instance, IMD 60 may be positioned for sensing cardiac electrical signals and for stimulating of a vagal nerve, phrenic nerve, hypoglossal nerve or the spinal cord, as examples.

The housing 62 of IMD 60 includes a header assembly 64 attached to a hermetically sealed housing 62. The housing 62 encloses the circuitry of IMD 60 and is generally electrically conductive but may be covered in part by an electrically insulating coating. A first, subcutaneous, sense electrode, A, is formed on the surface of the header assembly 64 and a second, subcutaneous, sense electrode, B, is formed by at least a portion of the housing 62. For example, electrode B may be an exposed portion of housing 62 when housing 62 is coated by an electrically insulating coating. The conductive housing electrode B may be directly connected with cardiac electrical signal sensing circuitry.

An electrical feedthrough extends through the mating surfaces of the header assembly 64 and the housing 62 to electrically connect the first sense electrode A with sensing circuitry enclosed within the housing 62. The electrical signals attendant to the depolarization and re-polarization of the heart 8 are referred to as the cardiac electrical signals are sensed across the sense electrodes A and B and include at least T-waves attendant to the ventricular repolarizations of heart 8. IMD 60 may be sutured to subcutaneous or submuscular tissue at a desired orientation of its electrodes A and B to the axis of the heart 8 to detect and record the cardiac electrical signals in a sensing vector A-B.

In some examples, the spacing between electrodes A and B may range from 60 mm to 25 mm. For instance, the electrode spacing may range from 55 mm to 30 mm, or from 55 mm to 35 mm. The volume of the IMD 60 may be three cubic centimeters or less, 1.5 cubic centimeters or less or any volume between three and 1.5 cubic centimeters. The length of IMD 60 may range from 30 to 70 mm, 40 to 60 mm or 45 to 60 mm and may be any length between 30 and 70 mm. The width of a major surface of IMD 60 may range from 3 to 10 mm. IMD 60 may have a thickness between 2 and 10 mm. These various example dimensions of IMD 60 are illustrative in nature and not intended to be limiting. IMDs that may employ the T-wave monitoring techniques disclosed herein may vary in size depending on the intended implant location, any therapy being delivered, and the volume required to enclose the circuitry and power source within the housing 62 for performing IMD functions, among other factors.

The sensing circuitry enclosed by housing 62 is configured to detect T-waves for monitoring T-wave morphology changes according to the techniques disclosed herein. Such sensing circuitry may include a pre-filter and amplifier, a rectifier, a sense amplifier, an analog-to-digital converter (ADC), a comparator and/or other components configured to receive cardiac electrical signals.

In general, the hermetically sealed housing 62 includes a battery or other power source, a processor and memory or other control circuitry that controls device operations and records cardiac electrical signals in memory registers, and a telemetry transceiver antenna and circuit that receives downlink telemetry commands from and transmits stored data in a telemetry uplink to an external device, such as device 50 of FIG. 1. The circuitry and memory may be implemented in discrete logic or a micro-computer based system with analog to digital conversion of sampled cardiac electrical signal amplitude values. One implantable cardiac signal monitor that can be modified in accordance with the presently disclosed techniques is described in U.S. Pat. No. 6,412,490 (Lee et al.), incorporated herein by reference in its entirety, as well as the cardiac monitors generally disclosed in U.S. Pat. No. 9,744,364 (Gordon, et al.) and U.S. 7,027,858 (Cao, et al.), both incorporated herein by reference in its entirety.

IMD 60 is shown as a leadless device with at least a pair of housing-based electrodes A and B for sensing cardiac electrical signals. In other examples, IMD 60 may include three or more housing based electrodes, e.g., including one sensing electrode pair and one stimulation electrode pair when IMD 60 is a neurostimulator. Additional electrodes may be located on the header assembly 64 and/or along housing 62. In still other examples, header assembly 64 may include one or more connector bores for receiving one or more leads extending from IMD 60, each carrying one or more electrodes. Electrodes carried by a lead extending from IMD 60 may be used to deploy electrodes at a target stimulation site and/or optimize sensing electrode position for sensing cardiac electrical signals, in particular T-waves. For instance, when IMD 60 cannot be positioned at an anatomical location that enables both stimulation of a target tissue and reliable sensing of T-waves, IMD 60 may be coupled to one or more leads for extending electrodes to a desired location for sensing cardiac electrical signals and/or to a target stimulation site. In some cases, electrodes carried by a lead extending from IMD 60 may be used for cardiac electrical signal sensing while housing based electrodes A and B are used for neurostimulation or vice versa. For instance, when IMD 60 is positioned inferior to heart 8, e.g., in an abdominal, pelvic or lower extremity location, or when IMD 60 is positioned superior to heart 8, e.g., in the neck or head, for delivering therapeutic stimulation pulses to a target tissue, a medical electrical lead may extend from IMD 60 toward the thoracic region to provide reliable sensing of T-waves. Such an IMD may be positioned for deep brain stimulation, stimulation for treatment of sleep apnea, stimulation for pain control, stimulation to treat incontinence, functional electrical stimulation, or other neurostimulation therapies. In various examples, any combination of housing based and/or lead based electrodes may be used sensing cardiac electrical signals including T-waves and delivering neurostimulation and/or muscle stimulation as need for a particular clinical application.

IMD 60 may not be configured to deliver a therapy that treats, alleviates or prevents the pathological event that is detected by T-wave monitoring by IMD 60. As described herein, IMD 60 may generate a notification that a pathological event is detected (present or predicted) that is transmitted to external device 50. External device 50 may be configured to communicate with a second medical device 70 (via communication link 72). Second medical device 70 may be an implantable or external medical device that is configured to deliver a therapy that addresses the detected pathological event. In response to receiving a pathological event notification, external device 50 may transmit a programming command to adjust therapy delivery, which may include turning therapy on, off or adjusting a therapy delivery control parameter. For example, the second medical device 70 may be an insulin pump. IMD 60 may detect hyperglycemia based on T-wave monitoring and transmit a notification to external device 50. External device 50 may transmit a dosage adjustment to second medical device 70 to adjust delivery of insulin. External device 50 may represent a system of more than one programmer or computer used to receive the pathological event notification, display information to the patient and/or a clinician, accept a therapy delivery programming change approved or preprogrammed by a clinician, display patient instructions approved or preprogrammed by the clinician, and/or transmit a programming command to the second medical device 70 to deliver a therapy to address the pathological event.

In other examples, IMD 60 may be configured to communicate directly with another medical device 70 to transmit a notification via a direct communication link 74. The second medical device 70 may start, stop or adjust therapy delivery in response to the pathological event detection notification. In various examples, the second medical device 70 may be a drug pump, neurostimulator, cardiac pacemaker or other device configured to deliver a therapy to the patient 3 that treats or prevents a pathological event being detected by IMD 60.

FIG. 3 is a conceptual diagram of an example configuration of a medical device that is configured to detect T-wave morphology changes for detecting or predicting a pathological event. The example shown in FIG. 3 corresponds to IMD 14 of FIG. 1 coupled to multiple electrodes 20, 22, 24, 26, 28, 30, 32, and 34 (electrodes 36 and 38 not shown in FIG. 3 for the sake of clarity) with housing 15 shown as an electrode. The circuitry shown in FIG. 3 is described with reference to the multi-chamber IMD 14 of FIG. 1, having sensing, pacing and cardioversion/defibrillation capabilities. However, it is to be understood that the aspects of the circuits and components shown and described in conjunction with FIG. 3 may be included in IMD 60 of FIG. 2 and modified as necessary to provide sensing and stimulation (when therapy delivery capabilities are included) for a different clinical application than cardiac electrical stimulation therapies. Furthermore, circuitry and components described in conjunction with FIG. 3 that is employed to provide the functionality disclosed herein for monitoring T-waves and detecting or predicting a pathological event based on T-wave changes may be included in an external medical device, e.g., a wearable device, which may or may not include therapy delivery capabilities. Such functionality includes establishing T-wave templates for multiple T-wave template conditions and detecting a pathological event based on changes in T-wave morphology that are independent of or different than changes in the T-wave morphology due to changes in the T-wave template conditions.

IMD 14 includes a control circuit 80, memory 82, therapy delivery circuit 84, a cardiac electrical signal sensing circuit 86 (also referred to herein as "sensing circuit 86"), telemetry circuit 88, sensor 96 and a power source 98. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Cardiac electrical signal sensing circuit 86 may include multiple sensing channels, e.g., an atrial sensing channel 87 and a ventricular sensing channel 89. Atrial sensing channel is configured to receive a cardiac electrical signal, e.g., via RA electrodes 20 and 22, for sensing atrial P-waves and producing an atrial EGM signal that may be passed to control circuit 80 for analysis by processor 92 for atrial rhythm and rate detection. A ventricular sensing channel 89 may receive a cardiac electrical signal, e.g., via RV electrodes 24 and 26 and/or CS electrodes 32, 34, 36 and 38 (only electrodes 32 and 34 are shown in FIG. 3 for the sake of clarity). Ventricular sensing channel 89 includes circuitry for detecting ventricular R-waves and T-waves and for producing a ventricular EGM signal that may be passed to control circuit 80 for use in detecting the ventricular rhythm and rate and for analyzing T-waves as described herein. When IMD 14 is a multi-chamber device, separate RV and LV sensing channels may be provided for sensing ventricular electrical signals from the respective RV electrodes 24 and 26 and CS electrodes 32, 34, 36 and 38.

Each atrial sensing channel 87 and ventricular sensing channel 89 may include a respective pre-filter and amplifier circuit including a high pass filter to remove DC offset, e.g., a 2.5 to 5 Hz high pass filter, or a wideband filter having a passband of 2.5 Hz to 100 Hz to remove DC offset and high frequency noise. The pre-filter and amplifier circuit may further include an amplifier to amplify a "raw" cardiac electrical signal that is passed to an ADC included in each sensing channel 87 and 89. The ADC may pass a multi-bit, digital EGM signal to control circuit 80 for use in detecting cardiac events and determining a patient's heart rhythm.

Control circuit 80 may identify T-waves from the ventricular EGM signal and generate T-wave templates for use in detecting changes in T-wave morphology indicative of a pathological event.

The digital signal from the ADC of each respective channel 87 and 89 may be passed to a rectifier and amplifier circuit included in sensing circuit 86, which may include a rectifier, bandpass filter, and amplifier for passing the filtered and rectified cardiac electrical signal to a respective cardiac event detector, e.g., an atrial event detector in the atrial channel 87 and a ventricular event detector in the ventricular channel 89.

The cardiac event detector of each respective channel 87 and 89 may include a sense amplifier, comparator or other detection circuitry that compares the incoming rectified, cardiac electrical signal to a cardiac event sensing threshold amplitude, which may be an auto-adjusting threshold. When the incoming signal crosses the sensing threshold amplitude the cardiac event detector produces a cardiac sensed event signal that is passed to control circuit 80. Ventricular sensed event signals may be passed from ventricular sensing channel 89 to control circuit 80 in response to a cardiac event detector sensing a ventricular sensing threshold crossing. Ventricular sensed event signals may be used by timing circuit 94 for scheduling ventricular pacing pulses and determining ventricular event intervals (between two consecutively received ventricular sensed event signals). Control circuit 80 may determine the ventricular rhythm from the determined ventricular event intervals, which may be in combination with an analysis performed by processor 92 of the ventricular EGM signal received from sensing circuit 86.

In some examples, ventricular channel 89 may include a dedicated T-wave detector for detecting T-waves from the ventricular signal received by ventricular channel 89. Ventricular channel 89 may include an R-wave channel having filtering properties and an R-wave detector for detecting R-waves and a separate, dedicated T-wave channel having filtering properties and a T-wave detector for detecting T-waves. The T-wave channel, when included, may have a lower frequency passband and lower sensing threshold amplitude than the R-wave channel to promote reliable detection and identification of T-waves. Sensing circuit 86 may generate a T-wave sensed event signal when the ventricular signal received by ventricular channel 89 crosses a T-wave sensing threshold, which may be required to be within a T-wave sensing window following an R-wave.

In other examples, a ventricular event detector of ventricular channel 89 may be used for detecting R-waves and T-waves. The ventricular sensing threshold may be set to a an initially high level, e.g., based on a percentage of a previously sensed R-wave peak amplitude, and gradually decrease to a minimum sensing threshold, referred to herein as the "sensitivity" and sometimes referred to as the "sensing floor." The sensitivity, generally set in millivolts, is the lowest amplitude at which a cardiac signal crossing results in a ventricular sensed event signal being produced by the ventricular event detector. The ventricular sensing threshold may decrease according to one or more decay rates, which may include step drops in amplitude, from the starting ventricular sensing threshold amplitude to the sensitivity setting. When the cardiac electrical signal received by ventricular channel 89 crosses the ventricular sensing threshold, a ventricular sensed event signal is produced and passed to control circuit 80. During normal R-wave sensing, ventricular sensing control parameters used by ventricular channel 89, such as the ventricular sensing threshold, sensitivity setting, threshold decay rate, and bandpass filtering of the received cardiac electrical signal, are generally set to avoid T-wave sensing due to T-waves crossing the ventricular sensing threshold as it decreases toward the programmed sensitivity setting. The ventricular sensing threshold is auto-adjusted so that the T-wave is highly unlikely to cross the ventricular sensing threshold and is not falsely sensed as an R-wave.

When ventricular sensing channel 89 does not include a dedicated T-wave detector, control circuit 80 may periodically, on a triggered or scheduled basis, adjust ventricular sensing control parameters to promote T-wave sensing to facilitate T-wave morphology monitoring. In some examples, the sensitivity setting of the ventricular channel 89 is decreased to intentionally cause T-wave sensing by the ventricular channel 89. In other examples, the starting ventricular sensing threshold amplitude and/or decay rate may be decreased in addition to or alternatively to the sensitivity setting. In still other examples, the adjustment to ventricular sensing control parameters for enabling T-wave sensing may include adjusting the high pass cut-off frequency or the bandpass frequency range of a bandpass filter of ventricular channel 89 to reduce attenuation of T-wave signals in the received cardiac electrical signal.

After adjusting ventricular sensing control parameters, both R-waves and T-waves may be sensed, resulting in a ventricular sensed event signal being passed to control circuit 80 each time an R-wave and each time a T-wave occurs. Control circuit 80 may be configured to identify T-waves from the ventricular sensed event signals received from ventricular channel 89 which correspond to both R-waves and T-waves. Techniques for identifying T-waves are described below and may generally include an analysis of ventricular event intervals between consecutively received ventricular sensed event signals, which correspond to both R-waves and T-waves. Analysis of consecutive ventricular event intervals between events sensed by ventricular channel 89 when the sensing control parameters are adjusted to promote T-wave sensing allows control circuit 80 to identify T-wave signals. In this way, T-waves may be acquired for generating T-wave templates and acquired during monitoring sessions for comparing to a previously established T-wave template for detecting T-wave morphology changes indicative of a pathological event.

Control circuit 80 may receive atrial sensed event signals from atrial sensing channel 87 each time the atrial event detector included in atrial sensing channel 87 senses an atrial P-wave due to an atrial sensing threshold crossing by the atrial signal received via electrodes 20 and 22. Atrial sensed event signals may be used by timing circuit 94 in scheduling atrial and/or ventricular pacing pulses and determining the atrial rate by determining atrial event intervals between consecutively received atrial sensed event signals. In some examples, the timing of sensed P-waves relative to ventricular sensed event signals received during adjusted ventricular sensing control parameter(s) may be used in identifying T-wave signals sensed by ventricular channel 89 and discriminating T-wave signals from sensed R-waves.

Control circuit 80 may include timing circuit 94 and processor 92. Control circuit 80 may receive atrial sensed event signals and ventricular sensed event signals and/or digital cardiac electrical signals from sensing circuit 86 for use in detecting cardiac rhythms and controlling therapy delivery functions. For example, atrial sensed events signals and ventricular sensed event signals may be passed to timing circuit 94 for inhibiting scheduled atrial or ventricular pacing pulses, respectively. Timing circuit 94 may set pacing escape intervals in response to a cardiac sensed event signal.

For example, an atrial pacing escape interval may be started in response to an atrial sensed event signal. A ventricular pacing escape interval may be started in response to a ventricular sensed event signal or an atrial sensed event signal. Expiration of the pacing escape interval causes therapy delivery circuit 84 to deliver a pacing pulse to the appropriate cardiac chamber via a pacing electrode vector selected from the available electrodes. If a cardiac event signal is received prior to expiration of the pacing escape interval, the time that has expired on the pacing escape interval timer or counter is determined as a cardiac event interval, e.g., an atrial event interval or ventricular event interval. The cardiac event intervals determined by timing circuit 94 may be used by processor 92 for detecting arrhythmias and, as described below, identifying T-wave signals.

Control circuit 80 may identify T-wave signals received from sensing circuit 86 and receive a digitized ventricular EGM signal including T-wave signals for analysis by processor 92 for generating T-wave templates and comparing identified T-waves to previously established T-wave templates. Processor 92 may compare differences between an identified T-wave and a T-wave template to criteria for detecting or predicting a pathological event, e.g., myocardial infarction, VT, VF, hypervolemia, hypovolemia, seizure, hyperglycemia, hypoglycemia, hyperkalemia, hypokalemia, drug over- or under-dosing or other event that causes changes in the T-wave morphology that are different than T-wave changes that may occur with non-pathological changes in a patient condition, such as heart rate or paced rhythm.

Control circuit 80 may retrieve programmable therapy delivery control parameters from memory 82, such as pacing rate as controlled by timing circuit and pacing pulse amplitude, pacing pulse width, and CV/DF shock energy, which are passed to therapy delivery circuit 84 for controlling electrical stimulation pulse delivery. In addition to providing control signals to therapy delivery circuit 84, control circuit 80 may provide sensing control signals to sensing circuit 86, e.g., atrial and ventricular sensing thresholds, sensitivity and sensitivity adjustments for T-wave sensing, and/or various blanking and refractory intervals applied to the cardiac electrical signal to control sensing of P-waves, R-waves and T-waves by the respective atrial channel 87 and ventricular channel 89.

Therapy delivery circuit 84 generates electrical pacing pulses that are delivered to the patient's heart via the available electrodes coupled to IMD 14, e.g., electrodes 20, 22, 24, 26, 28, 30, 32, 34, 36 and 38 and housing 15. Therapy delivery circuit 84 may include charging circuit 120, switching circuit 122 and an output circuit 124. Charging circuit 120 may include one or more holding capacitors that may be charged to a pacing pulse amplitude by a multiple of the battery voltage signal of power source 98 under the control of a voltage regulator. The pacing pulse amplitude may be set based on a control signal from control circuit 80. Switching circuit 122 may control when the holding capacitor of charging circuit 120 is coupled to the output circuit 124 for delivering the pacing pulse. For example, switching circuit 122 may include a switch that is activated by a timing signal received from timing circuit 94 upon expiration of a pacing escape interval and kept closed for a programmed pacing pulse width to enable discharging of the holding capacitor of charging circuit 120. The holding capacitor, previously charged to the pacing pulse voltage amplitude, is discharged across a selected electrode pacing vector through an output capacitor of output circuit 124 for the programmed pacing pulse duration. Output circuit may include multiple output capacitors and switching circuitry for selectively discharging the holding capacitor through a desired output capacitor and pacing electrode vector. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 80 for generating and delivering a pacing pulse.

Therapy delivery circuit 84 may include both high voltage holding capacitor(s) and low voltage capacitor(s) in charging circuit 120 when IMD 14 is capable of delivering high voltage CV/DF shock therapies in addition to cardiac pacing therapies. For example, a high voltage holding capacitor may be charged to a voltage corresponding to a programmed shock energy using a transformer. As such, charging circuit 120 may include a transformer to step up the battery voltage of power source 98 in order to achieve charging of a high voltage rated capacitor to a voltage that is much greater than the battery voltage. Charging of the high voltage capacitor (or a combination of capacitors) by charging circuit 120 may be performed under the control of processor 92, which receives feedback signals from therapy delivery circuit 84 for determining when the high voltage capacitor is charged to a voltage corresponding to a programmed shock energy. A charge completion signal may be passed from processor 92 to charging circuit 120 to terminate charging. One example of a high voltage charging circuit and its operation is generally disclosed in U.S. Pat. No. 8,195,291 (Norton, et al.), incorporated herein by reference in its entirety.

In some examples, control circuit 80 may respond to a pathological event detection by generating a patient or clinician alert. For example, therapy delivery circuit 84 may generate low amplitude electrical stimulation perceptible by the patient. Control circuit 80 may generate an audible alarm or vibration or control telemetry circuit 88 to transmit an alert notification to external device 50. Additionally or alternatively, control circuit 80 may respond to detection of a pathological event by controlling therapy delivery circuit to deliver a therapy.

While IMD 14 is shown as a cardiac stimulation device it is to be understood that therapy delivery circuit 84 may generate electrical stimulation pulses for neurostimulation, e.g., for deep brain stimulation, spinal cord stimulation, vagal nerve stimulation etc. For instance, an IMD performing the techniques disclosed herein may be configured as a deep brain stimulator so that therapy delivery circuit generates electrical stimulation pulses delivered to the brain via electrodes carried by an intracranial lead and coupled to therapy delivery circuit 84. In some instances, the T-wave changes are predictive of increased tachyarrhythmia risk. Atrial and/or ventricular pacing may be provided or adjusted. For example rates and/or patterns of pacing pulses may be adjusted to reduce arrhythmic risk. In some examples, overdrive pacing of the atria or ventricles may be provided when a change in T-wave morphology is detected that is predictive of VT or VF.

In other examples, therapy delivery circuit 84 may include a drug pump instead of or in addition to the electrical stimulation pulse generating circuitry as shown in the example of FIG. 3. Therapy delivery circuit 84 may be configured for delivering a pharmacological agent for treating a pathological event detected from a change in T-wave morphology. Therapy delivery circuit 84 may be coupled to a catheter or port for delivering a pharmaceutical agent intravenously, submuscularly or within a target tissue. Examples of drug therapies that may be delivered include a drug therapy for treating or preventing hypokalemia, hyperkalemia, epileptic seizure, or insulin shock based at least in part on T-wave monitoring using the techniques disclosed herein. Therapy delivery circuit 84 may be configured to deliver calcium, insulin, glucose, sodium bicarbonate, albuterol, a diuretic, patiromer, potassium, or anti-epileptic drugs, as examples.

Pacemaker 14 may include one or more sensors 96 for monitoring physiological signals of the patient other than the cardiac electrical signals sensed by sensing circuit 86. For example, IMD 14 may include a patient activity sensor 96 which may include a motion sensor such as an accelerometer for detecting motion of the patient caused by patient physical activity. A signal from activity sensor 96 passed to control circuit 80 may be analyzed by processor 92 for determining a metric of patient physical activity for use in controlling the pacing rate according to the patient's physical activity level, sometimes referred to as "rate responsive pacing." In some examples, processor 92 is woken up at predetermined time intervals to determine a patient activity metric, which may be determined by determining a threshold crossing count and/or integration of the motion sensor signal. For instance, processor 92 may be woken up at two second time intervals by control circuit 80 to determine an updated patient activity metric from the activity sensor signal. An updated activity metric may be used to determine an updated sensor indicated pacing rate, and adjust the pacing rate intervals accordingly. The motion sensor may be a multi-axis sensor with DC components that may be used in determining patient posture in addition to (or alternatively to) patient physical activity. The activity metric and/or patient body posture may be used as a T-wave template condition in some examples. T-wave templates may be generated for different patient activity metric levels or ranges, one or more patient body postures, or a combination thereof.

In other examples, IMD 14 may include other sensors of physiological conditions of the patient such as a blood pressure sensor, optical sensor for use in determining blood or tissue oxygen saturation, an acoustical sensor for sensing heart sounds, temperature sensor, pH sensor, or any combination thereof. In some examples, control circuit 80 may control therapy delivery circuit 84 and sensing circuit 86 to apply an impedance drive signal for monitoring a resultant impedance signal that may correlate to bioimpedance of tissue or a blood volume. For example, an impedance signal may be used to determine cardiac or thoracic or subcutaneous impedance for monitoring a fluid status (e.g., hypervolemia, hypovolemia, dehydration or fluid retention) of the patient or respiratory signals. A blood pressure signal may be used to estimate pulmonary artery diastolic pressure for monitoring the fluid status of the lungs in a patient with congestive heart failure. Processor 92 may determine a metric correlated to a patient condition from a sensor signal or combination of sensor signals for determining a state of the patient condition. T-wave morphology analysis may be performed in combination with analysis of one or more sensor signals from sensor(s) 96 for establishing T-wave template conditions and/or in detecting and confirming a pathological event.

T-wave morphology may change due to changes in a patient condition that are independent of a pathological event. Accordingly, in some examples, control circuit 80 is configured to determine a state of a patient condition based on a signal from signals from sensing circuit 86, sensors 96 and/or therapy delivered by therapy delivery circuit 84 and establish T-wave templates for two or more states of a patient condition, referred to as a T-wave template condition. A change in the state of the T-wave template condition may cause a non-pathological change in T-wave morphology that should not be detected as a pathological event. As such, a T-wave template may be established by control circuit 80 for each one of multiple T-wave template conditions. A sensed T-wave signal may be compared to the T-wave template corresponding to the T-wave template condition present at the time of sensing the T-wave so that pathological changes in T-wave morphology may be detected and discriminated from T-wave morphology changes due to changes in the T-wave template condition. Examples of T-wave template conditions include, but are not limited to, heart rate, paced or intrinsic heart rhythm, patient physical activity, patient posture, blood pressure, pH, oxygen saturation, body temperature, time of day, and cardiac, thoracic or subcutaneous impedance. In some examples, a T-wave template condition may be a time of day that corresponds to the time of taking oral medication that may alter T-wave morphology.

Changes in any of these conditions may be within a range of normal patient conditions not associated with a pathological event being monitored for, but T-wave changes may occur with changes in these T-wave template conditions. T-wave changes that occur with changes in normal conditions should not necessarily be detected as a change in T-wave morphology indicative of pathological event. The techniques disclosed herein may be used to discriminate between non-pathological changes in T-wave morphology due to non-pathological changes in a patient condition and changes in T-wave morphology that are indicative of a pathological event.

Memory 82 may include computer-readable instructions that, when executed by processor 92 of control circuit 80, cause control circuit 80 to perform various functions attributed throughout this disclosure to a medical device, e.g., IMD 14 or IMD 60. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media.

Power source 98 provides power to each of the other circuits and components of IMD 14 as required. Power source 98 may include one or more energy storage devices, such as one or more rechargeable or non-rechargeable batteries. The connection between power source 98 and control circuit 80 is shown, but connections between power source 98 and other circuits and components are not shown in FIG. 3 for the sake of clarity and are to be understood from the general block diagram of FIG. 3. For example, power source 98 may provide power to charging circuit 120 for charging a holding capacitor to a pacing voltage amplitude, current to switch 122 and other circuitry included in therapy delivery circuit 84 as needed to generate and deliver electrical stimulation pulses to the patient's heart. Power source 98 also provides power to telemetry circuit 88, sensing circuit 86 and sensor 96 as needed as well as memory 82.

IMD 14 may include a telemetry circuit 88 including a transceiver and antenna for transferring and receiving data, e.g., via a radio frequency (RF) communication link with an external programmer or home monitor, such as external device 50 shown in FIG. 1. Telemetry circuit 88 may be capable of bi-directional communication with external device 50 (FIG. 1), for example, when external device 50 is a programmer or home monitor used to transmit programming commands to IMD 14 and retrieve data from IMD 14. Cardiac electrical signals, marker channel data depicting the timing of cardiac event sensing and pacing, currently programmed parameters or other data may be transmitted by telemetry circuit 88. In particular, cardiac signal episodes including T-waves representative of detected pathological events may be stored in memory 82 and transmitted via telemetry circuit 88. Programmable control parameters and programming commands for controlling cardiac electrical signal sensing and cardiac pacing may be received by telemetry circuit 88 and stored in memory 82 for access by control circuit 80.

The functions attributed to a medical device herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. The operation of circuitry included a medical device as disclosed herein should not be construed as reflective of a specific form of hardware, firmware and software necessary to practice the techniques described. It is believed that the particular form of software, hardware and/or firmware will be determined primarily by the particular system architecture employed in the medical device and by the particular sensing and therapy delivery circuitry employed. Providing software, hardware, and/or firmware to accomplish the described functionality in the context of any modern pacemaker, given the disclosure herein, is within the abilities of one of skill in the art.

Figure 4:
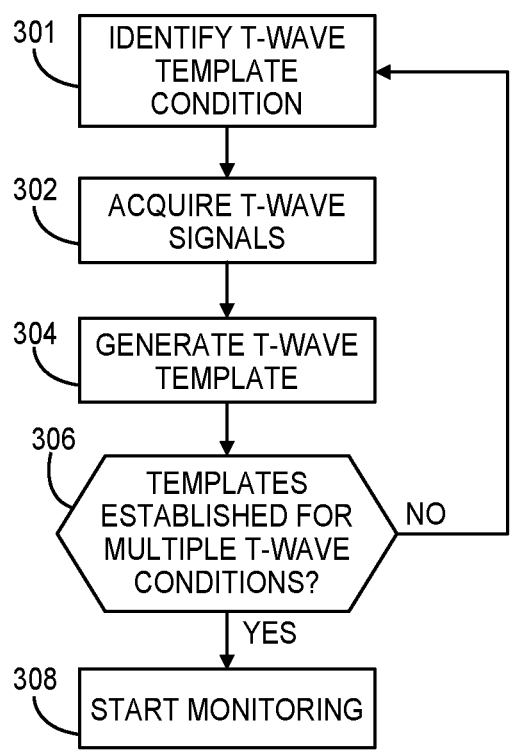
FIG. 4 is a flow chart of a method performed by a medical device for generating T-wave templates for multiple T-wave template conditions according to some examples.

FIG. 4 is a flow chart 300 of a method performed by a medical device, e.g., IMD 14 or IMD 60 of FIGS. 1 and 2, respectively, for generating T-wave templates for multiple T-wave template conditions according to some examples. The method of flow chart 300 may be performed at scheduled time intervals or triggered by the detection of a T-wave template condition at block 301. At block 301, control circuit 80 may identify a T-wave template condition by verifying the absence of ventricular tachyarrhythmia or other cardiac rhythm condition known to result in irregular myocardial repolarization (such as frequent atrial or ventricular ectopic beats) by analyzing the cardiac electrical signal and/or one more signals from sensor(s) 96. Examples of T-wave template conditions have been given above. In one example, the T-wave template condition identified at block 301 is heart rate. Multiple heart rate ranges may be defined over a normal range of expected heart rates of the patient, such as 45-65 beats per minute (bpm), 65-85 bpm, 85-105 bpm, and 105-125 bpm, and 125-145 bpm. Other rates and ranges may be defined in other examples. Since T-wave morphology may change with heart rate, in the absence of a pathological event, a T-wave template may be generated for multiple heart rate conditions. At block 301, control circuit 80 may determine the patient's heart rate based on the atrial sensed event signals and/or ventricular sensed event signals received from sensing circuit 86.

In another example, the T-wave template condition identified at block 301 is the paced heart rhythm. Paced heart rhythm conditions may include an intrinsic sensed (non-paced) rhythm during which both intrinsic atrial P-waves are sensed and intrinsic ventricular R-waves are sensed. A rhythm of atrial sensing and ventricular sensing is referred to as an AS-VS rhythm. Other paced rhythm conditions may include an atrial paced and ventricular sensed rhythm (AP-VS rhythm), an atrial sensed and ventricular paced rhythm (AS-VP rhythm) and an atrial paced and ventricular paced rhythm (AP-VP rhythm). Control circuit 80 may determine a paced rhythm condition at block 301 by determining whether sensed event signals are being received from sensing circuit 86 from one or both of atrial channel 87 and ventricular channel 89 and whether timing circuit 94 is controlling therapy delivery circuit 84 to deliver pacing pulses to one or both atrial and ventricular heart chambers. Since T-wave morphology may change with changes in the paced rhythm condition in the absence of a pathological event, different T-wave templates may be generated for multiple paced rhythm conditions.

In some examples, the T-wave template condition identified at block 301 may be a combination of conditions. For example, control circuit 80 may determine the combination of a heart rate and a paced rhythm condition as the T-wave template condition (as further described below in conjunction with FIG. 6). Other conditions or combinations of conditions of the patient may be determined using sensor(s) 96 for identifying a T-wave template condition, such as, with no limitation intended, an impedance condition, a blood pressure condition, a patient activity level, a patient posture, or any combination thereof.

At block 302, control circuit 80 controls sensing circuit 86 and processor 92 to acquire T-wave signals during the identified T-wave template condition. The control circuit 80 may acquire T-wave signals using any T-wave detection technique then store a digitized time segment of the ventricular EGM signal encompassing the T-wave. In some examples, the T-wave is detected by controlling ventricular channel 89 of sensing circuit 86 to decrease the ventricular sensitivity setting to a relatively low voltage amplitude compared to the sensitivity setting normally used for sensing R-waves. For example, the sensitivity may be reduced from 0.25 millivolts to 0.125 millivolts. The sensitivity setting may be decreased until cardiac sensed event signals are received from ventricular channel 89 that are identified as T-waves. A method for detecting T-waves to facilitate the acquisition of T-wave signals at block 302 is described below in conjunction with FIG. 5.

A predetermined number of T-wave signals are acquired during the T-wave template condition at block 302 and may be stored in memory 82, e.g., in a rolling buffer configured for storing the digitized signals. At least one T-wave signal is acquired at block 302 and multiple T-wave signals, e.g., 2 to 8 T-wave signals or other predetermined number of T-wave signals may be acquired. At block 304, processor 92 generates a T-wave template for the identified T-wave template condition using the acquired T-wave signals. The acquired T-waves may be temporally aligned using a fiducial point of each acquired T-wave signal. For example, a maximum peak amplitude may be used to align each signal to determine an ensemble average of the acquired T-wave signals by averaging the aligned signal sample points of the predetermined number of T-wave signals.

At block 306, control circuit 80 may determine if a minimum number of T-wave templates have been established for enabling T-wave morphology monitoring for detecting a pathological event. For example, T-wave templates for each one of multiple heart rate ranges, or at least the most frequently occurring heart rate ranges may be established. In other examples, T-wave templates are required for multiple types of paced heart rhythms or at least the most frequently occurring paced heart rhythms for a given patient. After the first T-wave template is generated, control circuit 80 may return to block 301 to repeat the process of generating a T-wave template for one or more additional T-wave template conditions. In some examples, monitoring for a change in T-wave morphology indicative of a pathological event may begin when a single T-wave template for one T-wave template condition has been established.

When an adequate number of T-wave templates are established, e.g., at least one, two or more templates, control circuit 80 may start monitoring T-waves at block 308 according to a monitoring protocol for detecting a pathological event. Methods for T-wave monitoring are described below in conjunction with FIG. 7. While T-wave monitoring is ongoing, additional T-wave templates may be generated according to the method of flow chart 300 as additional T-wave template conditions are identified at block 301 for which a template has not yet been generated. Furthermore, when T-wave signals are compared to a stored T-wave template and found to be within a threshold difference of the T-wave template, newly acquired T-waves may be used to update a stored T-wave template. In other examples, T-wave templates may be periodically re-generated using the method of flow chart 300 to replace a previously established template stored in memory 82, e.g., on a regularly scheduled basis or upon user command.

Figure 5:
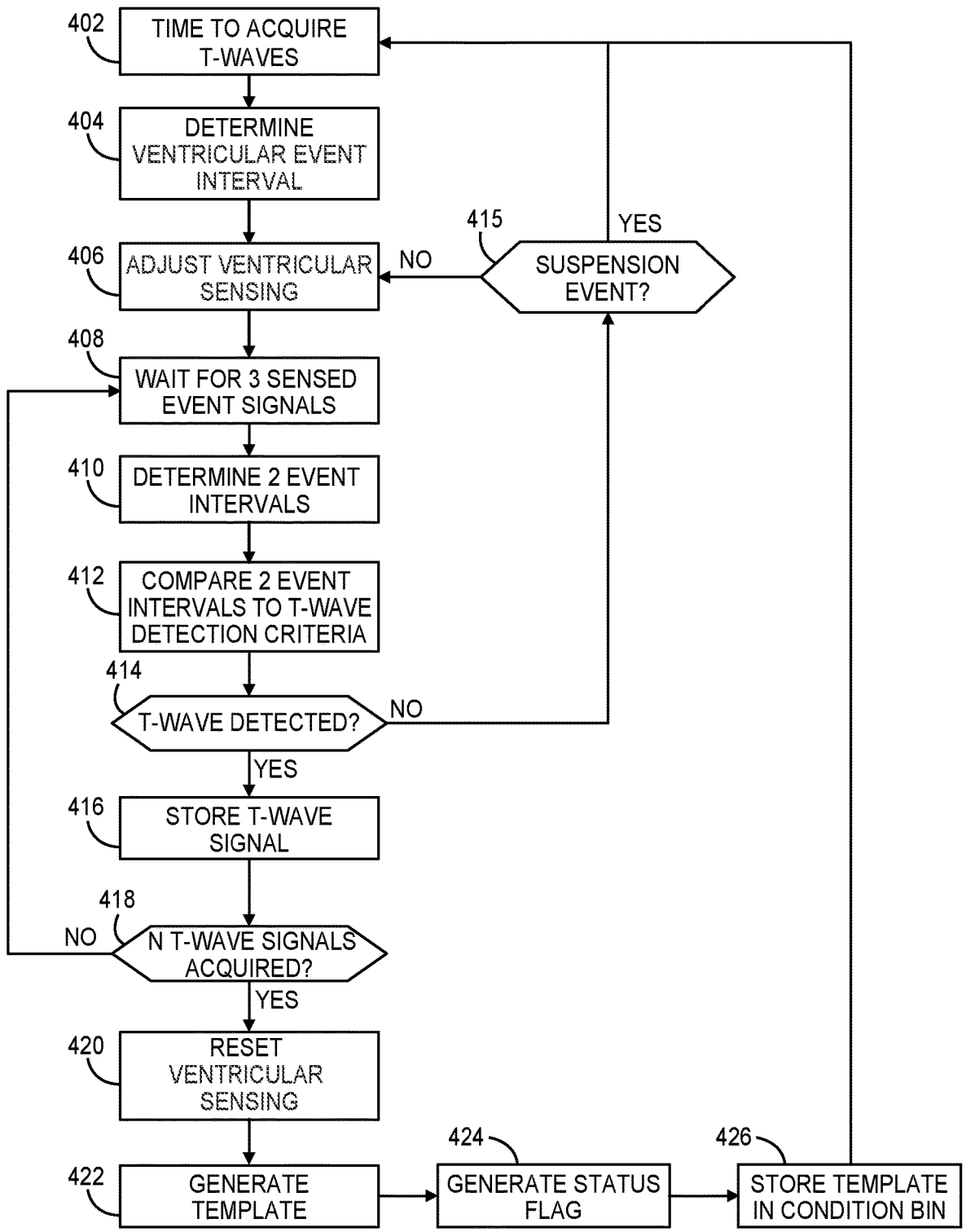
FIG. 5 is a flow chart of a method for acquiring T-wave signals according to one example.

FIG. 5 is a flow chart 400 of a method for acquiring T-wave signals according to one example. At block 402, control circuit 80 determines that it is time to acquire T-waves for template generation. As discussed above, this determination may be made based on a scheduled time interval or time of day or in response to detecting a T-wave template condition for which a T-wave template has not yet been generated, needs to be completed due to an insufficient number of T-wave signal segments acquired for generating the template, or needs updating. In addition to identifying a T-wave template condition and/or scheduled time for T-wave template generation, control circuit 80 may determine that other conditions that may conflict with T-wave template generation are not present. For example, control circuit 80 may verify that a ventricular tachyarrhythmia is not being detected or other IMD operations that may be of higher priority or preclude reliable T-wave acquisition are not underway.

In response to determining that it is time for T-wave signal acquisition at block 402, control circuit 80 determines a ventricular event interval at block 404. The ventricular event interval may be a paced or sensed ventricular event interval. The ventricular event interval may be an average ventricular event interval determined from several, e.g., 3 to 8, ventricular event intervals each determined between two consecutively received ventricular sensed event signals (or delivered ventricular pacing pulses). The ventricular event interval may have already been determined at block 402 as part of identifying a T-wave template condition that includes heart rate. If not, the ventricular event interval is determined at block 404 as a reference ventricular rate interval for use in detecting T-waves during T-wave signal acquisition.

At block 404, control circuit 80 adjusts the ventricular sensing control parameters to enable T-wave sensing. In one example, control circuit 80 decreases the ventricular channel sensitivity setting of sensing circuit 86. For example, ventricular sensitivity may be set to 0.3 millivolts during normal R-wave sensing to avoid T-wave sensing. During T-wave signal acquisition, the ventricular sensitivity setting may be gradually reduced to cause ventricular channel 89 to be more sensitive to detecting lower amplitude T-waves. The ventricular sensitivity setting may be reduced in a stepwise manner until T-waves are intentionally being oversensed, resulting in ventricular event signals produced by ventricular sensing channel for both R-waves and T-waves. The ventricular sensitivity setting may be decreased at block 406 from an initial value, e.g., 3 millivolts, by a 0.5, 0.25 or 0.1 millivolt decrement, as examples.

In various examples, one or more of the ventricular sensitivity, starting ventricular sensing threshold amplitude, sensing threshold decay rate, and/or filtering bandpass may be adjusted at block 406 to promote T-wave sensing. For cardiac electrical signals sensed using intracardiac electrodes (e.g., as shown in FIG. 1), the high pass cut-off frequency for R-wave sensing may be in the range of 10 to 20 Hz. The high pass cut-off frequency may be reduced to be in the range of 5 to 15 Hz, for example, to promote T-wave sensing. For cardiac electrical signals sensed using extracardiovascular electrodes, e.g., subcutaneous or submuscular electrodes as shown in FIG. 2 or skin electrodes for an external medical device, the high pass filter cut-off frequency for R-wave sensing may be in the range of 5 to 10 Hz, which may be reduced to a high pass cut-off frequency of 1 to 5 Hz, for example, to promote T-wave sensing.

During T-wave signal acquisition, the high pass filter cut-off frequency for R-wave sensing may be gradually reduced to cause ventricular channel 89 to be more sensitive to detecting lower amplitude T-waves. The high pass filter cut-off frequency may be reduced in a stepwise manner until T-waves are intentionally being oversensed, resulting in ventricular event signals produced by ventricular sensing channel for both R-waves and T-waves. The high pass filter cut-off frequency may be decreased at block 406 from an initial value, e.g., 13 Hz, by a 2, 4, or 6 Hz decrement, as examples.

When the ventricular sensing control parameter(s) are adjusted to cause T-wave sensing, the rate of ventricular sensed event signals will double since both an R-wave and a T-wave will be sensed during each ventricular cycle. Accordingly, as the ventricular sensing control parameters are adjusted at block 406, control circuit 80 may wait to receive three ventricular sensed event signals from the ventricular channel 89 at block 308. The two event intervals defined by the three consecutively received ventricular sensed event signals are determined at block 410. These two event intervals may be compared to T-wave detection criteria by control circuit 80 at block 412.

If the second ventricular sensed event signal of the three consecutive sensed event signals is a T-wave, preceded and followed by R-waves, the first event interval defined by the three consecutively received ventricular sensed event signals is an R-T interval and second event interval is a T-R interval. The sum of these two intervals is an RR interval, which should approximately match the ventricular event interval determined at block 404. Accordingly, control circuit 80 may compare the first interval to an expected R-T interval for the known heart rate based on the ventricular event interval determined at block 404. The second interval may be compared to an expected T-R interval, and/or the sum of the first and second intervals may be compared to the ventricular event interval determined at block 404. In some examples, all three of these comparisons may be made at block 412 for verifying that the second ventricular sensed event signal is a T-wave. For example, the sum of the two intervals may be required to be within a predetermined percentage, e.g., 10% or 20% of the ventricular event interval determined at block 404. The first interval may be required to within an expected R-T interval percentage range of the ventricular event interval determined at block 404, e.g., 35% to 45% of the ventricular event interval. The second interval may be required to be within an expected T-R interval range, e.g., 55%-65% of the ventricular event interval. In other examples, at least one or two of these comparisons may be required to meet predefined timing criteria for detecting the second ventricular sensed event signal as a T-wave at block 414. Thus, the timing of the second ventricular sensed event signal between the immediately preceding and immediately following ventricular sensed events may be used to verify that the second sensed event signal is a T-wave at blocks 412 and 414.

In some instances, when three consecutive ventricular sensed event signals are received, the first event may be a T-wave and/or the last event may be a T-wave, with the R-wave occurring as the second event. In this case, the sum of the two event intervals should still match the ventricular event interval determined at block 404. The first event interval, a T-R interval in this case, should match an expected T-R interval percentage of the ventricular, and the second event interval, an R-T interval, should match an expected R-T interval percentage of the ventricular determined at block 404. As such, the criteria applied at block 412 may include matching the first event interval to either of the expected T-R or R-T time interval range that is based on the ventricular event interval determined at block 404, the second event interval matching the other of the expected T-R or R-T time interval range and the sum of the two intervals matching the ventricular event interval determined at block 404.

When criteria for detecting at least one of the three consecutively received ventricular sensed event signals as a T-wave are not satisfied ("no" branch of block 414), control circuit 80 may verify that a suspension event has not occurred at block 415. A suspension event may be a change in the T-wave template condition for which T-waves are being acquired. A different T-wave template condition may be identified and the process of acquiring T-wave signals for one condition may be terminated with the process of acquiring T-wave signals for another condition being started at block 402.

In other examples, a suspension event is detected at block 415 based on the two event intervals that failed to meet T-wave detection criteria at block 414. In some instances, the three consecutive events may still be R-waves due to the sensitivity setting or other ventricular sensing control parameters not being decreased enough to start sensing T-waves. In other instances, the three consecutively sensed events may represent a fast ventricular rhythm or include an ectopic beat, e.g., a premature ventricular contraction (PVC). Accordingly, control circuit 80 may apply criteria at block 415 for determining if the three events represent a suspension event that causes T-wave signal acquisition to be temporarily suspended. For example, if the T-wave detection criteria were not met at block 414, each of the first event interval and the second event interval examined at block 412 may match the ventricular event interval determined at block 404, indicating three consecutive R-waves were sensed. In this case, the sensitivity setting (or other ventricular sensing control parameters) is still too high to sense T-waves. If the two event intervals match the ventricular event interval and/or the sum of the two event intervals matches twice the ventricular event interval, a suspension event is not detected at block 415 ("no" branch). Control circuit 80 returns to block 406 to adjust ventricular sensing control parameter(s) and repeats the process of blocks 408 through 414.

However, if the two event intervals and/or sum of the two event intervals do not correspond to a T-wave detection (R-T-R sequence or T-R-T sequence) or to three consecutive R-waves occurring at the expected ventricular event interval, one, two or all three cardiac sensed event signals may correspond to a tachyarrhythmic event or an ectopic event. For example, one or both of the two event intervals determined at block 410 may be very short, less than an expected R-T interval and/or T-R interval, or the sum of the two event intervals may be a threshold percentage less than the expected ventricular event interval suggesting a fast ventricular rhythm. In other instances, the ratio of the first interval to the second interval may represent the presence of a PVC. A short first interval followed by a long second interval may be indicative of an R-wave followed by a PVC followed by a long pause. This short-long interval pattern that does not meet T-wave detection criteria at block 414 or expected ventricular event interval criteria may be identified as a suspension event at block 415. At other times, a PVC may be followed by an R-wave at a long pause and another R-wave at the expected ventricular event interval resulting in a long-normal interval pattern. Accordingly, criteria for detecting a PVC or other arrhythmic events may be applied at block 415 for detecting a suspension event. In other examples, when criteria for detecting a T-wave are not met and criteria for verifying three consecutive R-waves are not met at block 415, a suspension event is detected at block 415 without applying other criteria to the two time intervals for identifying a particular arrhythmic pattern of the two intervals.

When a suspension event is detected, control circuit 80 may suspend T-wave signal acquisition and return to block 402 to wait for the T-wave template condition and any other required T-wave signal acquisition conditions to be identified again before resuming T-wave signal acquisition procedures. In some examples, control circuit 80 may identify a PVC based on the pattern of a short-long, long-short or long-normal interval pattern at block 415. In this case, T-wave signal acquisition may not be suspended but the events including a PVC may be ignored and skipped during the T-wave acquisition process. Instead of suspending T-wave acquisition, control circuit 80 may return to block 406 to reduce the ventricular sensitivity setting until T-waves are detected (without detecting a PVC). If a PVC is identified at block 415 and T-waves have already been identified prior to the PVC indicating the ventricular sensitivity is adequately high for sensing T-waves, control circuit 80 may return to block 408 to wait for the next three sensed event signals for identifying another T-wave.

When a T-wave is detected at block 414 based on the event interval criteria applied at block 412, control circuit 80 stores a T-wave signal segment of the ventricular EGM signal received from sensing circuit 86 corresponding to the identified T-wave. The ventricular EGM signal received from ventricular channel 89 may be buffered in memory while event interval analysis is performed for detecting a T-wave. Once a cardiac sensed event signal is identified as a T-wave, a segment of the buffered ventricular EGM signal encompassing the T-wave signal may be stored at block 416. The T-wave signal may be a non-rectified, wide bandpass filtered signal (e.g., 0.5 to 100 Hz wide bandpass filtered signal) to preserve "raw" T-wave signal morphology. In other examples, the T-wave signal segment may be a relatively narrower bandpass filtered and/or rectified signal that is used for generating features or metrics of the T-wave signal morphology as a T-wave template.

Storing the T-wave signal at block 416 may include detecting a maximum peak amplitude of the T-wave by control circuit 80 (or sensing circuit 86 when the ventricular channel includes a peak detector for use in setting a starting R-wave sensing threshold amplitude). The T-wave signal segment stored at block 416 may include a predetermined time interval (or number of digital sample points) before and after the maximum peak amplitude. For example, the ventricular EGM signal may be stored starting from 50 ms to 150 ms before the T-wave maximum peak amplitude to 50 ms to 150 ms after the T-wave maximum peak amplitude.

After storing the T-wave signal segment at block 416, control circuit 80 may determine at block 418 if an adequate number of T-waves have been acquired for generating a T-wave template for the current T-wave template condition. A minimum of two, three, four, five or other predetermined number of acquired T-wave signals may be required to generate the T-wave template. In some cases, particularly when T-wave signal acquisition has been suspended, a portion of the T-wave signals required for generating a usable template may have been acquired previously, but additional T-wave signal segments are still required to complete the T-wave template. In this case, the number N of T-wave signals required at block 418 may be fewer than the total number of T-wave signal segments required to complete a usable T-wave template. For example, three T-wave signal segments may be have been acquired during a previous T-wave signal acquisition session that was suspended due to a change in the T-wave template condition or other suspension event at block 415. The process of flow chart 400 may be performed until two more T-wave signals are acquired for the given T-wave template condition, as determined at block 418. When a total of five T-wave signal segments are required for completing a usable T-wave template, the five T-waves signals acquired over more than acquisition session may be used to generate the T-wave template.

In some examples, a template may be generated when at least two T-wave signals have been acquired as determined at block 418, which may be fewer than the number of T-wave signals required to generate a complete template. The template is generated at block 422 by averaging the acquired T-wave signals that may be temporally aligned based on a fiducial point of the T-wave signal segments. For example, the starting sample point of each T-wave signal segment may be aligned. Alternatively, the maximum peak amplitude sample point of each T-wave signal segment may be aligned. The aligned T-wave signal segments are averaged to generate the template at block 422.

The process of generating a template at block 422 may include comparing the T-wave signal segments to each other (and/or to a previously generated incomplete T-wave template). Each T-wave signal segment used to generate the T-wave template may be required to match all of the other T-wave signal segments (or previously generated incomplete T-wave template) within predetermined matching criteria in order to be used for generating the template. Relatively homogenous T-wave signals may be selected for generating the T-wave template. The determination of whether a T-wave signal sufficiently matches other T-wave signal segments (or previously generated T-wave template) may include a comparison of predetermined features, such as maximum peak amplitude, T-wave width, T-wave slope, or overall waveform morphology as determined using a wavelet transform analysis or other waveform matching techniques. In some cases, one or more acquired T-wave signals may be discarded and not used for generating the T-wave template at block 422. In this case, an initial T-wave template may be generated using the T-wave signals found to be matching but may be considered an incomplete template that is not yet usable for T-wave morphology monitoring.

Control circuit 80 may generate a template status flag at block 424 indicating whether the generated template is ready for use in monitoring T-wave morphology for detecting a pathological event. When the required number of T-wave signal segments is used for generating the template at block 422, e.g., five segments in one example, the status flag generated at block 424 may indicate that the template is complete. In some examples, however, a template may be generated from fewer than a minimum number of T-wave signals required for generating a usable T-wave template, e.g., when some T-wave signals are discarded. If additional T-wave signals are required, control circuit 80 may generate a status flag at block 424 indicating that the T-wave template is incomplete. The status flag may additionally indicate the number of additional T-wave signals that are required to complete the T-wave template. For example, if a T-wave template is generated at block 422 using two T-waves, but five T-waves are required for generating a usable T-wave template, the status flag generated at block 424 may indicate that the T-wave template is incomplete and three more T-wave signals need to be acquired.

In this way, control circuit 80 may determine that T-wave signal acquisition is needed at block 402 when a T-wave template condition is identified for which a T-wave template status flag indicates an incomplete template. The control circuit 80 may acquire the number of additional T-wave signals needed according to the T-wave status flag for completing the T-wave template. In the foregoing example, when two T-wave signals have already been used for generating an incomplete T-wave template, control circuit 80 may perform the process of flow chart 400 until three more T-wave signal segments have been acquired as determined at decision block 418, with the number "N" T-wave signals acquired being based on the template status flag. Initially N is set to the required number of T-wave signals for generating a usable template, e.g., five T-wave signals and is adjusted down as T-wave signals are acquired during one or more acquisition sessions.

The template generated at block 422 is stored in memory 82 at block 426 in a memory bin corresponding to the T-wave template condition identified at block 402, along with the status flag generated at block 424. In this way, if the T-wave signal acquisition process is suspended at block 415, the control circuit 80 may use T-wave signals acquired up until the suspension for generating a T-wave template and restart acquiring additional T-wave signals when the same T-wave template condition is identified again at block 402. When a T-wave template is incomplete, the T-wave signals acquired so far may be stored for the corresponding T-wave template condition in addition to or instead of generating an incomplete template from the T-wave signals acquired so far. A template may be generated from all of the individual T-wave signals once the required number of T-wave signals has been acquired for completing the T-wave template.

In other examples, T-wave signals acquired after the initial, incomplete template is generated may be averaged with the incomplete template. In this case, individual T-wave signal segments acquired after the initial, incomplete T-wave template is generated from fewer than the required number of acquired T-wave signals may be compared to the incomplete T-wave template to ensure that the later T-wave signal segments are within a predetermined percentage of the initial template. In some cases, an initial, incomplete template may need to be discarded if the required number of T-wave signal segments sufficiently matching the initial template cannot be obtained within a threshold interval of time or after attempting to acquire a threshold number of matching T-wave signals. A change in the T-wave due to medication or another underlying condition may cause the normal T-wave morphology for the given T-wave template condition to change such that an older template may need to be discarded and a new template generated from more current, recently acquired T-wave signal segments.

Figure 6:
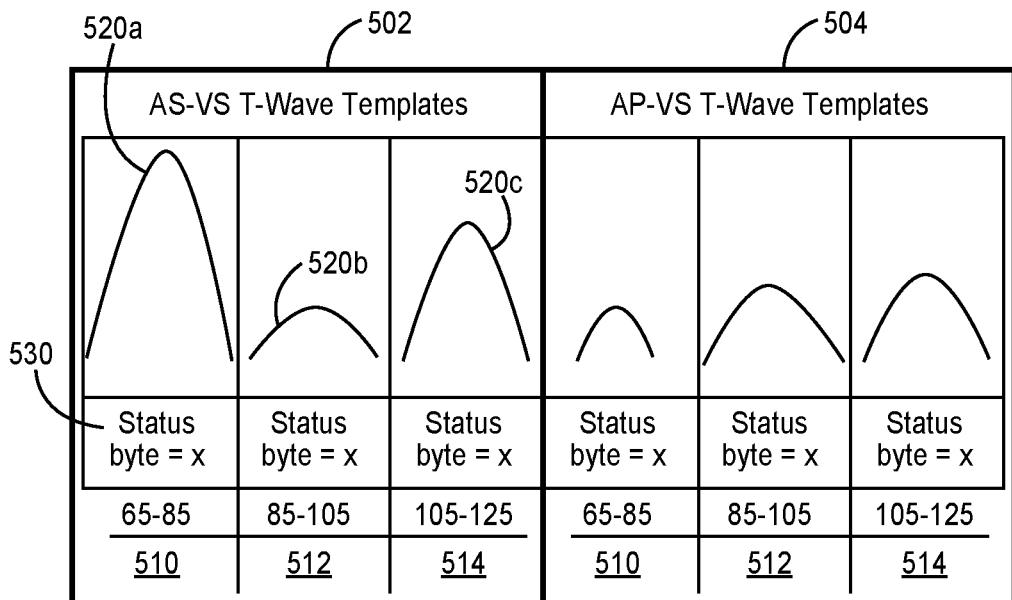
FIG. 6 is a conceptual diagram of T-wave template storage bins that may be included in memory of a medical device for storing T-wave templates for multiple T-wave template conditions.
Figure 6:
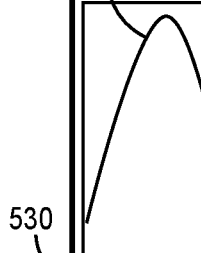
Figure 6:
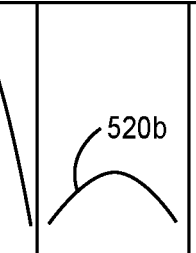
Figure 6:
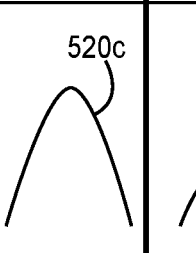
Figure 6:
Figure 6:
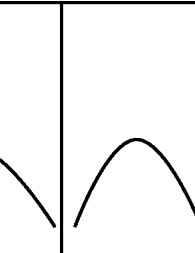
Figure 6:
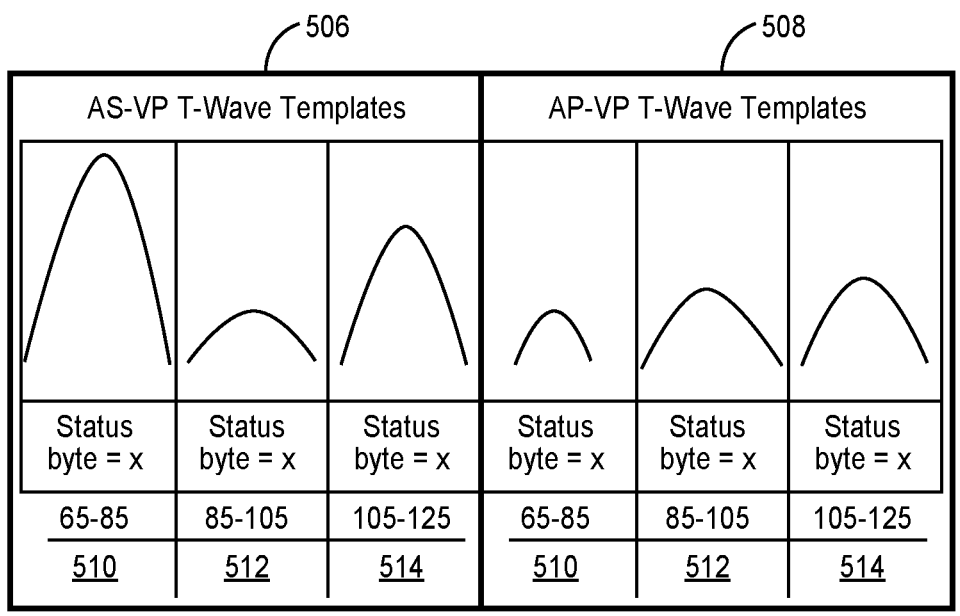
Figure 6:
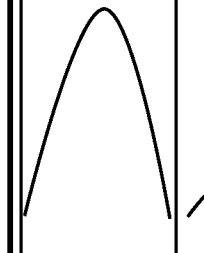
Figure 6:
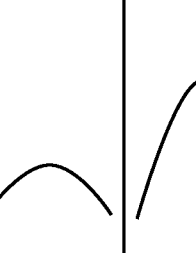
Figure 6:
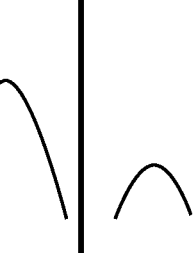
Figure 6:
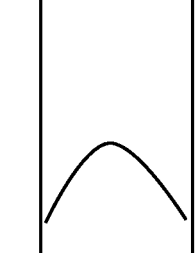

FIG. 6 is a conceptual diagram 500 of T-wave template storage bins that may be included in memory 82 for storing T-wave templates for multiple T-wave template conditions. Memory 82 may include multiple storage bins that correspond to multiple T-wave template conditions. Each bin is used for storing a T-wave template generated during the respective T-wave template condition. In the example shown a total of twelve bins are provided including three heart rate range bins 510, 512 and 514 for each of four paced rhythm conditions 502, 504, 506 and 508 for a total of twelve T-wave template conditions. Each T-wave template condition is a combination of a heart range 510, 512 or 514 and paced rhythm condition 502, 504, 506 or 508. Control circuit 80 is configured to identify each T-wave template condition represented by a storage bin and generate a T-wave template for the T-wave template condition, e.g., using the techniques described above in conjunction with FIG. 5.

As illustrated, a different T-wave template 520a, 520b and 520c is generated for each respective heart rate range 510, 512 and 514 during the paced rhythm condition of an intrinsic AS-VS rhythm 502. T-wave templates are generated for each respective heart rate range 510, 512 and 514 for each of the other three paced rhythm conditions of AP-VS rhythm 504, AS-VP rhythm 506 and AP-VP rhythm 508 for the total of twelve stored T-wave templates.

Each storage bin may include the digitized T-wave template, e.g., templates 520a-c, a T-wave template condition label, e.g., the combination of the paced rhythm condition of AS-VS, AP-VS, AS-VP, or AP-VP and heart rate range, and a template status flag 530. As described above, the template status flag 530 may indicate whether the template stored in that T-wave template condition bin is complete or incomplete and may indicate how many additional T-wave signals are needed to complete the T-wave template. A complete status flag indicates the template is ready to be used for T-wave monitoring. An incomplete status may indicate that the template is not ready to be used for T-wave monitoring. T-wave monitoring for detecting a pathological event may be performed using the available complete T-wave templates in some examples. In other examples, control circuit 80 waits for all T-wave template storage bins to have a complete status flag before starting T-wave monitoring for pathological event detection. The T-wave status flag may additionally or alternatively indicate that the T-wave template needs to be updated. Templates may be updated on a periodic basis, for example once a week, once a month or other selected schedule. If the status flag 530 indicates updating is needed, control circuit 80 may respond by initiating T-wave signal acquisition using the method FIG. 5 the next time the corresponding T-wave template condition is identified.

Each T-wave template, e.g., templates 520a-520c, is shown conceptually as a waveform in FIG. 6 which may be used for waveform morphology matching with a T-wave during monitoring. The T-wave waveform may be stored as a digitized, raw T-wave signal with wide bandpass filtering, e.g., 0.5 to 100 Hz bandpass filtering, and without rectification to retain T-wave characteristics. However, each T-wave template may include features derived from the T-wave signal in addition to or alternatively to the digitized T-wave signal waveform. T-wave templates may include, with no limitation intended, T-wave amplitude, T-wave slew rate, T-wave polarity, T-wave width, T-wave area, T-wave symmetry/asymmetry, QT interval, and/or ST segment amplitude or elevation. T-wave symmetry may be determined as the ratio of an area, width or sum of sample point amplitudes occurring before the T-wave peak amplitude to the respective area, width or sum of sample point amplitudes occurring after the T-wave peak amplitude.

In some examples, T-wave template features that are stored in a T-wave template condition bin may require analysis of multiple T-waves acquired during the given T-wave template condition. For example, QT interval variability, T-wave alternans, or other T-wave features that exhibit beat-to-beat variation when a pathological event is present or imminent may be determined using multiple T-wave signals. A metric of the variation in a T-wave feature may be determined and stored as a part of the T-wave template for a given T-wave template condition. The same metric may be determined during T-wave monitoring and compared to the stored template value. A change in the metric, such as an increase in QT interval variability or evidence of T-wave alternans may be evidence of a pathological event.

While the example in FIG. 6 includes two specific heart rhythm related T-wave template conditions, i.e., heart rate and paced rhythm, it is to be understood that multiple T-wave template conditions, with each condition having one or more levels or states of the associated condition, may be defined. Other examples of T-wave template conditions that may be defined with corresponding levels or states include but are not limited to: time of day, body temperature, body posture (e.g., upright, non-upright, prone, supine, side lying etc.), bioimpedance, intrinsic atrial rhythm (e.g., sinus rhythm or atrial fibrillation or atrial tachycardia), and QRS morphology (e.g., QRS width, QRS amplitude, QRS slew rate). Various template bins may be configured in memory 82 that may each represent a single patient condition (e.g., non-upright posture) or multiple combinations of two or more patient conditions.

For instance, a T-wave template may be established for a non-upright body posture to account for any normal T-wave changes that may occur when the patient is lying down compared to upright positions. This template for a non-upright body posture may be used for T-wave morphology comparisons when a non-upright posture is detected and may be independent of other T-wave template conditions. In other examples, a T-wave template may be stored for a non-upright posture and resting patient physical activity level. This template could be stored in addition to the templates represented in FIG. 6, which may be applied when non-upright body posture is detected for the respective heart rate and paced rhythm condition. Any patient condition or physiological signal that is detectable or monitored by the medical device based on one or more sensor signals or therapy delivery circuits implemented in the medical device may be used in defining a T-wave template condition.

Figure 7:
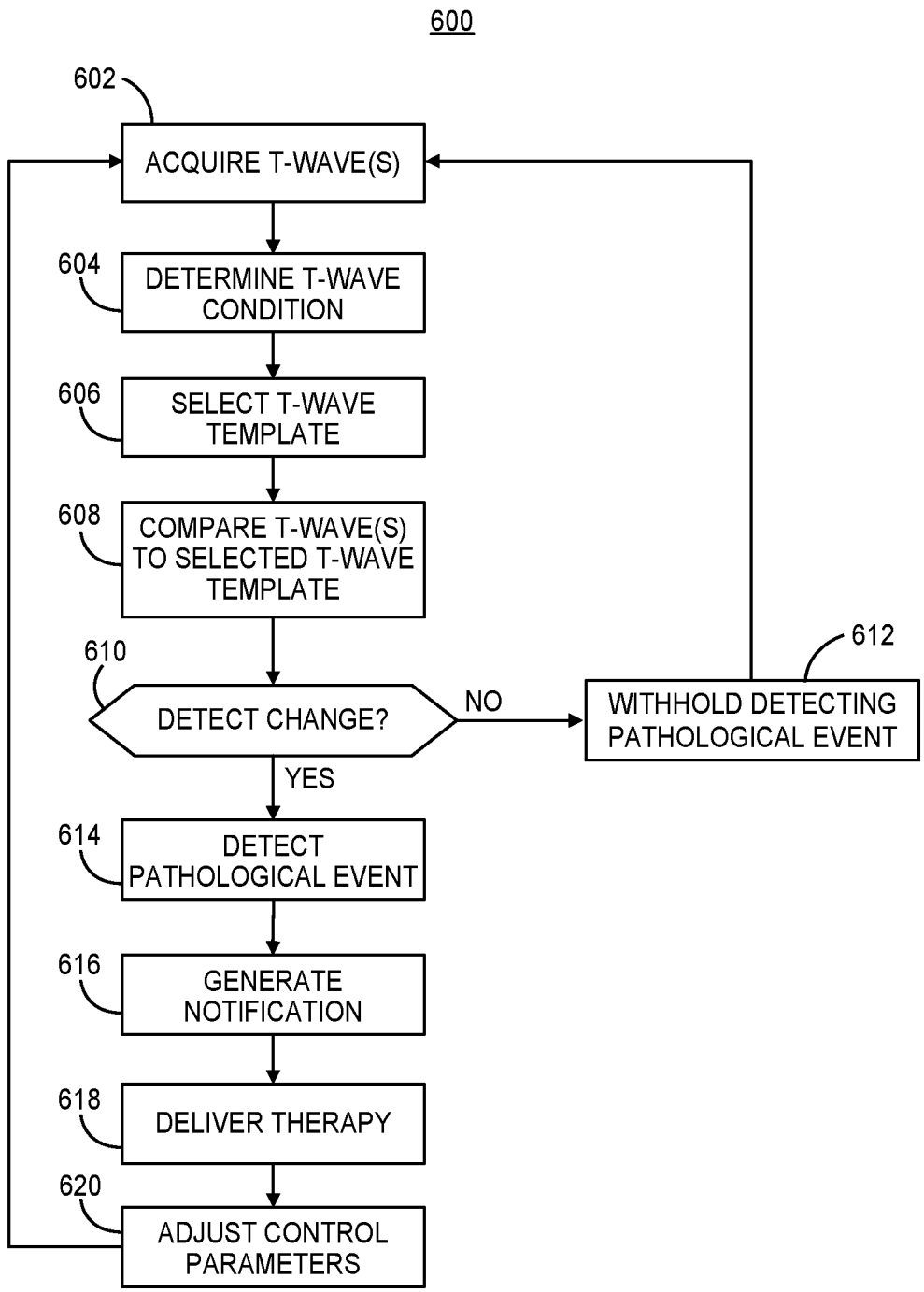
FIG. 7 is a flow chart for monitoring for changes in T-wave morphology for detecting a pathological event.

FIG. 7 is a flow chart 600 for monitoring for changes in T-wave morphology for detecting a pathological event. At block 602, control circuit 80 acquires T-waves according to a monitoring protocol. T-wave signals may be acquired on a scheduled basis, e.g., once per minute, once per hour, once per day or another scheduled time interval. The frequency of acquiring T-waves for morphological analysis may be set according to the pathological event being monitored or according to a schedule tailored to specific patient need. For example, a patient prone to have seizures during sleep may acquire T-waves more frequently during night time hours, e.g., every five minutes, and less frequently during day time hours, e.g., once per hour. In a patient being monitored for hypo- or hyperkalemia, T-waves may be acquired hourly, every four hours, or twice daily as examples. In still other examples, T-waves may be acquired every N cardiac cycles, for example every $20^{th}$ cardiac cycle throughout the day.

In some examples, T-wave signal acquisition at block 602 may be triggered by control circuit 80 in response to detecting a change in another signal, such as a change in heart rate, detection ectopic beats, a change in patient activity or posture, reduced activity for a threshold period of time, change to a non-upright posture, a change in blood pressure, or a change in impedance, as examples.

The T-waves acquired at block 602 may be acquired using the techniques for acquiring T-waves for establishing a T-wave template as described above in conjunction with FIG. 5. For example, the sensitivity of the ventricular channel 89 may be reduced until a T-wave is detected based on the analysis of two consecutive sensed event intervals. A required number of T-waves for detecting a pathological event may be defined such that at least 3, 5, 8, 12 or other predetermined number of T-waves are acquired at block 402. The T-waves may be acquired during consecutive cardiac cycles or during non-consecutive cycles. For instance, during T-wave acquisition for pathological event monitoring, a T-wave signal may be acquired on every $8^{th}$, $20^{th}$, $40^{th}$ or other selected number of ventricular cycles by reducing the ventricular channel sensitivity setting for one (or more) cardiac cycle(s). The ventricular channel sensitivity setting (and/or other ventricular sensing control parameter) required to sense T-waves may be known from the adjustments made during T-wave signal acquisition for T-wave template generation. Therefore, the ventricular sensing control parameter(s) may be adjusted directly to a setting that results in T-wave sensing in one step to acquire T-waves at block 602.

The current T-wave template condition present during the T-wave signal acquisition at block 602 is determined at block 604. In some examples, control circuit 80 may confirm that all T-waves acquired at block 602 are acquired during the same, single T-wave template condition. Using the example of FIG. 6, control circuit 80 may confirm that all T-waves acquired at block 602 are acquired within a single heart rate range and paced rhythm condition so that all of the acquired T-waves can be compared to a single T-wave template for reliably detecting a change in T-wave morphology due to a pathological event. If the heart rate or paced rhythm condition changes during the T-wave acquisition, control circuit 80 may wait for T-wave condition identified at block 604 to return to restart acquisition of T-waves until a minimum required number of T-waves for detecting a pathological event have been acquired during one single T-wave template condition.

Alternatively, the T-waves acquired at block 602 may each be flagged with the current T-wave template condition determined at block 604 for that cardiac cycle. Each acquired T-wave may be compared to a corresponding T-wave template based on the identified current T-wave template condition present at the time of the T-wave acquisition. In this way, changes in one or more patient conditions that may affect T-wave morphology may be accounted for by comparing each acquired T-wave to the appropriate T-wave template corresponding to the currently identified T-wave template condition present during a T-wave signal acquisition.

At block 606, one or more T-wave templates are selected as needed for comparison to the acquired T-waves so that each acquired T-wave signal can be compared to the appropriate T-wave template stored for the T-wave template condition(s) determined at block 604. At block 608, each of the acquired T-waves is compared to a respective T-wave template matching the T-wave template condition present during acquisition of each given T-wave. In some examples, a relatively small number of T-waves acquired during one T-wave template condition may be sufficient for detecting a pathological event (or conversely determining that the pathological event is not occurring or predicted). For example, as few as three to five T-waves acquired during one T-wave template condition may be compared to the template stored for that condition. If a change in the T-wave morphology is not detected at block 610, the pathological event is not detected at block 612. In some instances, acquisition of T-waves at block 602 is triggered in response to another signal indicating that a pathological event is suspected. For example, a change in cardiac rhythm may indicate a change in blood potassium levels. A change in a blood pressure or impedance signal may indicate a change in patient fluid status, e.g., dehydration or fluid retention or congestion. A glucose monitor may indicate an abnormal blood glucose level. When a change in another sensor signal indicates that a pathological event is suspected, but a change in T-wave morphology is not detected at block 610, the pathological event detection may be withheld at block 612.

If a change in T-wave morphology from a stored T-wave template is detected ("yes" branch of block 610), the pathological event is detected in response to the comparison at block 608. The comparison made at block 608 may require comparing one or more features of the acquired T-wave signals to the corresponding T-wave template. One or more of a peak amplitude difference, slope difference, width difference, area difference, and/or overall waveform morphology matching score, e.g., using a wavelet transform analysis, may be determined between an acquired T-wave signal and the corresponding T-wave template. Each of these differences and/or morphology matching score may be compared to a respective change threshold to detect a change in T-wave morphology at block 610. The comparisons made at block 608 and the change thresholds applied at block 610 may be selected and predefined according to the type of pathological event that is being monitored for and may be tailored to a specific patient. For example, in some patients, T-wave inversion, S-T segment depression, S-T elevation, or T-wave alternans may be correlated to the occurrence of epileptic seizures. An increase in T-wave amplitude, increase in leading slope, and/or a narrowing of T-wave width may occur with hyperkalemia. An increase in T-wave peak amplitude or T-wave asymmetry may indicate hyperglycemia. A decrease in T-wave amplitude and widening of the T-wave width may occur with hypoglycemia. Accordingly, one or more features may be established as a comparative feature for detecting or predicting the pathological event being monitored for.

Some pathological events may occur gradually or over a relatively longer period of time, e.g., a change in fluid status (edema, hypervolemia, hypovolemia, etc.), hypo- or hyperkalemia, or hypo- or hyperglycemia, as opposed to a sudden acute event such as epileptic seizure or myocardial infarction. As such, for some more slowly evolving pathological events, control circuit 80 may detect a pathological event when a T-wave morphology change is detected over a minimum period of time. A T-wave change compared to a T-wave template may be required to be detected at block 610 for multiple consecutive or non-consecutive (X of Y) T-wave signal monitoring time periods. For example, if T-waves are acquired every four hours (or other scheduled time interval) at block 602, a pathological event may be detected or predicted at block 614 when a T-wave change is detected at block 610 for at least 2, 3, 4 or other predetermined number of the scheduled T-wave monitoring sessions.

When the T-waves acquired at block 602 are determined to be acquired during more than one different T-wave template condition (block 604), which may be during one or more scheduled or triggered monitoring sessions, control circuit 80 selects the appropriate T-wave template for comparison to each respective T-wave acquired under the corresponding condition. In some examples, in order to detect a pathological event, control circuit 80 may be required to detect a change in T-wave morphology for multiple T-wave template conditions. For instance, control circuit 80 may detect a pathological event at block 614 when a T-wave change is detected for at least two or more different T-wave template conditions at block 610, which may be detected during one or more T-wave monitoring sessions. In this case, a minimum required number of T-waves may be acquired at block 602 for each one of multiple T-wave template conditions identified at block 604 to enable comparisons between T-waves and multiple, corresponding T-wave templates. In order to detect a change in T-wave morphology at block 610, control circuit 80 may apply criteria for detecting T-wave morphology changes to at least two different sets of acquired T-waves and corresponding T-wave templates. The pathological event may be detected when T-wave(s) acquired during at least one T-wave template condition do not match the corresponding T-wave template. In some examples, when T-waves are acquired for multiple T-wave conditions, T-waves that do not match one corresponding T-wave template may be sufficient evidence for the pathological event to be detected, even if T-waves for other T-wave template conditions do match their corresponding template.

In some cases, a preliminary detection of a pathological event may be made at block 614 in response to a T-wave morphology change being detected for one T-wave template condition. An initial patient notification or warning may be provided at block 616 in some examples. However, control circuit 80 may continue to acquire T-waves during additional T-wave template conditions as needed for making additional comparisons under multiple T-wave template conditions before confirming detection of the pathological event. When the pathological event is detected at block 614, control circuit 80 may generate a notification at block 616 that the pathological event is detected or predicted and/or deliver a therapy at block 616.

Some patients may be indicated for monitoring for more than one pathological event. For instance, a diabetic patient being monitored for hyper- and hypoglycemia may also be prone to seizures or ventricular tachyarrhythmias. As such, the process of FIG. 7 may be implemented to monitor for two or more pathological events concomitantly in a given patient. The process of FIG. 7 may be performed according to two or more different schedules or monitoring protocols concomitantly to monitor for two or more different pathological events. Alternatively, the process of FIG. 7 may be performed according to one monitoring schedule or protocol to simultaneously monitor for two or more different pathological events.

T-wave templates may be generated and stored according to the method of FIG. 5 that may include specific features that are known to change when a specific pathological event is being detected. For example, T-wave templates may be established for detecting hyper- and hypoglycemia that include T-wave amplitude and T-wave width, while different T-wave templates may be established for detecting or predicting seizure that include ST segment elevation and T-wave polarity. The T-wave templates established for detecting two or more different pathological events may be established for multiple T-wave template conditions as described above, which may be defined differently for each pathological condition being monitored for.

In other examples, one T-wave template may be stored for each T-wave template condition but each T-wave template may include all T-wave features that need to be examined for detecting all pathological events being monitored for. For example, one T-wave template that includes T-wave amplitude, T-wave width, ST segment elevation, and T-wave polarity may be stored for multiple T-wave template conditions to enable monitoring for both insulin shock and epileptic seizure.

At block 610, various thresholds and detection criteria may be applied to the comparisons made at block 608 for the detection of two or more different pathological events. For example, T-wave amplitude and width differences determined at block 608 may be compared to thresholds for detecting or predicting insulin shock at block 610 and ST segment elevation and T-wave polarity comparisons made at block 608 may be compared to thresholds or criteria for detecting or predicting seizure at block 610. Depending on which set of criteria are satisfied at block 610, a specific pathological event may be detected at block 614.

At block 616, control circuit 80 may generate an alert or notification, which may be transmitted by telemetry circuit 88, in response to detecting the pathological event. The notification may be specific to the pathological event detected so that the patient is aware of what steps to take, e.g., per physician instructions. Different notifications may be generated based on the pathological event that is detected when multiple pathological events are being monitored for. For instance, a diabetic patient may be provided with a medical device to monitor T-waves for detecting or predicting insulin shock but may also experience other pathological events, such as seizures, hyper- or hypokalemia, VT or VF, etc. As such, the T-wave change detected at block 610 may be specific to a pathological event that is being monitored for, and the subsequent notification generated at block 616 may notify the patient of the particular event that is detected or predicted.

In various examples, upon detecting the pathological event, control circuit 80 may store the T-wave signal data and any corresponding EGM signal, therapy delivery data, and/or other sensor signal data concurrent with the event. Among the signals and/or metrics that may be recorded with the detected T-wave morphology change information are patient body posture, patient physical activity metric, body temperature, QRS features (width, area, slew rate etc.), atrial rhythm, the T-wave template condition(s), or any other signal or condition that is being monitored by the medical device, along with the time and date stamp. In some examples, the medical device detecting the pathological event may be configured to deliver a therapy at block 618 in response to detecting the pathological event for treating or alleviating the event. For example, control circuit 80 may control therapy delivery circuit 84 to deliver a cardiac pacing or neurostimulation therapy in response to detecting a pathological cardiac event or a pathological neurological event. In other examples, a drug therapy may be delivered by therapy delivery circuit 84 in response to detecting the pathological event.

In another example, bundle branch block is detected at block 614 in response to detecting a change in T-wave morphology. In response to detecting bundle branch block, a cardiac resynchronization therapy (CRT) control parameter may be adjusted at block 618. CRT may be turned on and/or an atrioventricular (AV) or VV pacing interval may be adjusted to promote ventricular mechanical synchrony during bundle branch block. Since the T-wave morphology change that led to the detection of bundle branch block may be altered or normalized during CRT, CRT may be periodically suspended to check T-wave morphology to determine if the bundle branch block is no longer present, in which case the CRT may be turned off. As such, in some examples, acquisition of T-waves at block 602 may require withholding of a therapy that is delivered to treat, alleviate or prevent the pathological event being detected to determine if the pathological event has terminated and subsequently turning off or otherwise adjusting the therapy.

In some cases, detection of the T-wave signal change predicts that a pathological event is going to occur but is not yet occurring. In this case, a preventative therapy may be delivered by therapy delivery circuit 84 or by another medical device in communication with the medical device predicting the pathological event. For instance, when a T-wave change is detected that is predictive of VT or VF, overdrive pacing therapy may be delivered by therapy delivery circuit to prevent the onset of the VT/VF. The time of the detected change in T-waves may be stored in memory 82, along with any preventative therapy delivered, any subsequent VT/VF detection made and therapy delivered after VT/VF delivery for reporting to a clinician via telemetry circuit 88. External device 50 (FIG. 1) may generate a report and/or timing diagram on display 54 depicting the time of detected T-wave changes and a subsequent occurrence of a pathological event.

In some examples, control circuit 80 may adjust one or more control parameters used for sensing cardiac electrical signals and/or delivering therapy at block 620 in response to detecting the pathological event based on T-wave signal changes. For example, if an increase in T-wave amplitude is detected due to a pathological event, control circuit 80 may adjust ventricular sensing control parameters used by ventricular channel 89 to avoid T-wave oversensing until the pathological event subsides. For example, control circuit 80 may increase the ventricular sensitivity setting, increase a starting ventricular sensing threshold amplitude, adjust a decay rate of the ventricular sensing threshold amplitude, and/or adjust a cutoff frequency of the bandpass filtering of the cardiac electrical signal received by ventricular channel 89 to attenuate the T-wave signal. In this way, T-wave oversensing interference with R-wave sensing for detection of ventricular arrhythmias and/or controlling ventricular pacing therapies may be avoided. A patient implanted with IMD 14 for delivering CRT for a cardiac condition, for example, may experience an increase in T-wave amplitude due to hyperkalemia or hyperglycemia. The increase in T-wave amplitude may result in oversensing of T-waves by ventricular channel 89 and interfere with proper delivery of the CRT therapy. In some cases, T-wave oversensing may be difficult to avoid when a high amplitude, peaked T-wave is present due to a pathological event, making reliable R-wave sensing a challenge. In this situation, control circuit 80 may temporarily withhold a therapy that relies on R-wave sensing and/or temporarily withhold detection of a ventricular tachyarrhythmia that relies on R-wave sensing until the T-wave change is no longer detected.

As such, adjustment to ventricular sensing control parameters may be performed at block 620 in order to reduce the likelihood of oversensing T-waves by ventricular channel 89 in the presence of T-wave changes due to a pathological event. Additionally or alternatively, an adjustment to a cardiac pacing and/or cardiac arrhythmia detection control parameter may be made at block 620 to avoid interference of T-wave oversensing with therapy delivery and/or ventricular tachyarrhythmia detection. Control circuit 80 may adjust sensing and/or therapy delivery control parameters to avoid interference of T-wave oversensing with other medical device functions due to changes in T-wave morphology in the presence of the pathological event.

In other examples, control circuit 80 may adjust therapy delivery control parameters at block 620 to reduce the likelihood of the pathological event recurring. For instance, when the medical device performing the T-wave monitoring is an insulin pump and the detected pathological event is a hypoglycemic event, adjustments to the daily insulin dosage may be made to avoid a future insulin shock event. Accordingly, the response to detecting a pathological event may include generating a direct response to the event, e.g., an alert and/or therapy to alleviate the event (blocks 616 and 618), and/or adjusting a therapy control parameter toward preventing the pathological event from recurring at block 620. The therapy may be delivered by therapy delivery circuit 88 or by another medical device. The notification generated at block 616 may be a signal transmitted by telemetry circuit 88 directly to another medical device (e.g., device 70 in FIG. 2) configured to deliver therapy to treat, alleviate or prevent the detected pathological event. The response to detecting the pathological event may further include an adjustment to other medical device control parameters at block 620 that are not directly related to detecting, treating or preventing the detected pathological event but improve cardiac signal sensing operations and/or therapy delivery operations of the medical device in the presence of T-wave changes due to the pathological event.

Figure 8:
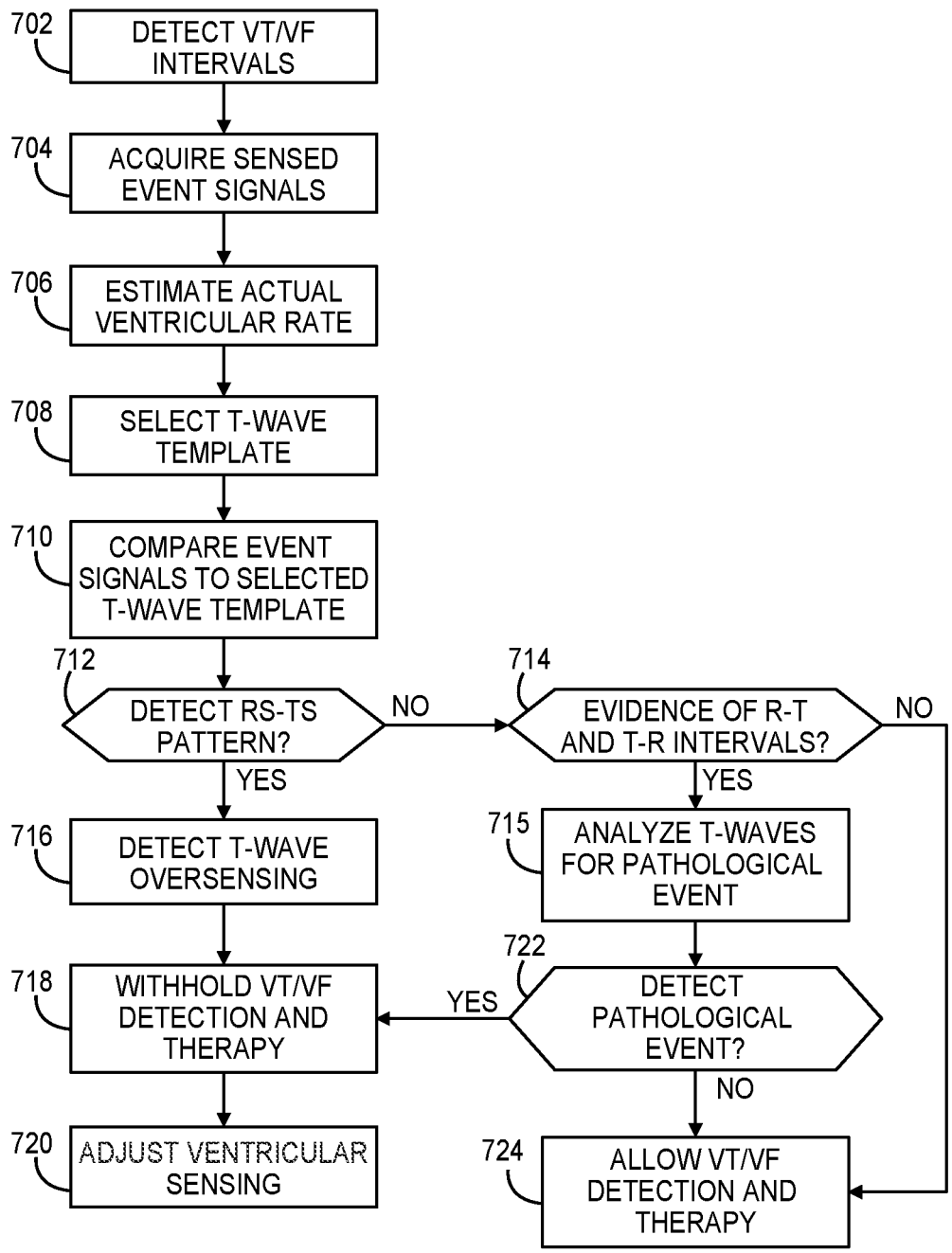
FIG. 8 is a flow chart for monitoring T-wave morphology by a medical device to detect T-wave oversensing according to another example.

FIG. 8 is a flow chart 700 for monitoring T-wave morphology by a medical device to detect T-wave oversensing according to another example. T-waves may be oversensed as false R-waves by ventricular channel 89 of sensing circuit 86. In particular, T-waves may be oversensed when the T-wave morphology changes due to other pathological events, which may cause an increase in T-wave amplitude. T-wave oversensing may potentially lead to a false ventricular tachyarrhythmia detection. When a false ventricular tachyarrhythmia is detected, an inappropriate ventricular tachycardia (VT) or ventricular fibrillation (VF) therapy may be delivered, such as a CV/DF shock. In order to avoid false detection of VT or VF, control circuit 80 may analyze T-wave signals by comparing them to an appropriate T-wave template for detecting T-wave oversensing.

In order to detect non-sinus VT or VF, control circuit 80 receives ventricular sensed event signals from sensing circuit 86, which may correspond to both true R-waves and false R-waves when T-wave oversensing occurs. Timing circuit 94 may time out the interval between consecutively received ventricular sensed event signals to determine ventricular event intervals. Control circuit 80 is configured to detect ventricular tachyarrhythmias by comparing each ventricular event interval to a VT detection interval threshold and a VF detection interval threshold. Each ventricular event interval that is less than a VT or VF detection interval is counted as a VT or VF interval. In some examples, a combined count of VT and VF intervals may be determined. When a threshold number N of VT or VF intervals out of M consecutive ventricular event intervals is detected, VT or VF may be detected by control circuit 80.

Control circuit 80 may be configured to detect a ventricular tachyarrhythmia rate of sensed ventricular events that is greater than a tachyarrhythmia detection rate threshold. As shown in FIG. 8, at block 702, control circuit 80 may determine when a threshold number of VT or VF intervals are detected that is less than the number of VT/VF intervals required for detecting VT or VF. For example, if 18 VT/VF intervals are required to detect VT or VF, control circuit 80 may determine when the count of VT or VF intervals, or a combined count of VT and VF intervals, reaches 8 VT/VF intervals at block 702. Control circuit 80 may be configured to analyze ventricular sensed event signals for detecting T-wave oversensing prior to the VT/VF interval count reaching a number of intervals (NID) to detect VT or VF.

At block 704, an EGM signal segment is acquired for each one of multiple ventricular sensed events that are consecutively sensed by ventricular channel 89 after the threshold number of VT/VF intervals are detected. In other examples, waveforms of the sensed ventricular events included in the threshold number of VT/VF intervals detected at block 702 may be buffered in a circulating buffer in memory 82 so that they are available for analysis by control circuit 80 upon the threshold number of VT/VF intervals being reached. The sensed event signals may be acquired by detecting a maximum signal peak following each ventricular sensing threshold crossing and storing the digital EGM signal segment for a predetermined number of milliseconds, e.g., 100 to 200 milliseconds, before and after the maximum signal peak. The duration of the acquired sensed event signal segments may correspond to the duration of each of the stored T-wave templates previously established, e.g., according to the method of FIG. 5 described above.

At block 706, control circuit 80 estimates a "true" or actual heart rate assuming T-wave oversensing is occurring. Control circuit 80 may be configured to estimate an actual heart rate that is less than the tachyarrhythmia detection rate based on the rate of the sensed ventricular events. In some examples, control circuit 80 may determine a median or mean ventricular event interval of the VT/VF intervals detected at block 702 and double the event interval assuming every other sensed event is an oversensed T-wave. The doubled event interval corresponds to the estimated actual heart rate. In other examples, control circuit 80 determines the ventricular sensed event interval for each sensed event signal acquired at block 704 and doubles the sensed event intervals to estimate the actual ventricular rate beat by beat.

Other techniques may be used to estimate the actual ventricular rate at block 706 based on the rate of sensed ventricular events. For example, control circuit may determine the time duration of a moving window of a predetermined number of ventricular sensed event intervals. Control circuit 80 may divide the total time duration by half the predetermined number assuming two ventricular events (one R-wave and one T-wave) are being sensed per cardiac cycle. For example, 24 consecutive ventricular event intervals may be determined and summed. The sum may be divided by 12 to determine an average "true" ventricular event interval assuming T-wave oversensing is occurring. Other techniques may be implemented to estimate a "true" ventricular event interval or true ventricular rate based on the ventricular sensed event signals and the assumption that T-wave oversensing is occurring at least intermittently during the rate analysis period, resulting in one-half or lower fraction of the sensed ventricular events being T-waves.

At block 708, control circuit 80 selects the appropriate T-wave template(s) stored for the heart rate condition(s) that includes the estimated "true" ventricular rate(s) for each of the sensed event signals acquired at block 704. After selecting an appropriate T-wave template for a matching heart rate condition at block 708 for each acquired sensed event signal, control circuit 80 compares each sensed event signal to the corresponding selected T-wave template at block 710. At block 712, control circuit 80 determines if T-wave oversensing criteria are met. In the example shown, control circuit 80 determine if T-wave oversensing criteria are met by comparing each one of a series of consecutively acquired sensed event signals to determine if an alternating pattern of sensed R-waves and sensed T-waves (RS-TS pattern) is detected (block 712). The RS-TS pattern is detected when every other sensed event signal matches the T-wave template stored for the corresponding "true" heart rate estimated at block 706 and the intervening sensed event signals do not match the corresponding T-wave template for the estimated "true" heart rate condition.

In one example, a T-wave template match is identified at block 710 when the difference in waveform area of the sensed event signal and the selected T-wave template is less than 20%, less than 15%, or 10% or less, as examples. If the area difference is more than a threshold percentage, the event may be marked as an R-wave. If the area difference is less than the threshold percentage, the event may be marked as a T-wave. In other examples, a peak amplitude, signal width, slope, wavelet matching score or other sensed event signal features may be compared to the analogous T-wave template features for determining a match, marked as a T-wave, or a non-match, marked as an R-wave.

After analyzing a series of consecutive sensed event signals, if the pattern of sensed events is marked as an alternating RS-TS pattern, "yes" branch of block 712, T-wave oversensing is detected at block 716. In other examples, other T-wave oversensing criteria may be required in addition to or instead of detecting an alternating RS-TS pattern at block 712. For instance, T-wave oversensing criteria may be satisfied at block 712 when at least one or more, e.g., a threshold percentage, of the sensed ventricular event signals match the respective T-wave template(s) selected based on the estimated actual heart rate. Control circuit 80 withholds VT/VF detection and any pending or scheduled VT/VF therapies at block 718 in response to detecting T-wave oversensing. When T-wave oversensing is detected (block 716), control circuit 80 may adjust ventricular sensing control parameters at block 720, e.g., by increasing the sensitivity setting of ventricular channel 89, to reduce the likelihood of T-wave oversensing. Other adjustments of ventricular sensing control parameters that may reduce the likelihood of T-wave oversensing may include increasing the starting ventricular sensing threshold amplitude (e.g., as a higher percentage of the R-wave amplitude), adjusting a decay rate of the sensing threshold amplitude, and/or adjusting the cutoff frequencies of a bandpass filter of ventricular channel 89.

When the sensed event pattern is not a pattern of alternating T-wave template matches, "no" branch of block 712, control circuit 80 may analyze consecutive sensed event intervals to detect evidence of R-T and T-R intervals that sum to the estimated "true" heart rate at block 714. Two consecutive event intervals that meet T-wave detection criteria, as described above in conjunction with FIG. 5 may provide evidence of oversensed T-waves, even when the candidate T-wave signals do not match the T-wave template(s) stored for the estimated "true" heart rate condition. T-wave oversensing may be occurring but the T-wave morphology may be altered from the stored template due to the presence of a pathological event, precluding detection of the RS-TS pattern at block 712. T-wave morphology may change due to a pathological event resulting in T-wave oversensing with the T-wave morphology not matching the stored T-wave template for the heart rate condition identified at block 706. In this case, pairs of consecutive event intervals may be analyzed based on the estimated "true" heart rate to identify candidate T-waves as described above in conjunction with FIG. 5.

When two consecutive event intervals meet T-wave detection criteria based on an ventricular event interval corresponding to the estimated "true" heart rate at block 714, control circuit 80 may analyze candidate T-wave signals identified at block 714 based on the sensed event interval analysis for detecting a pathological event at block 715. The event signal stored for an identified candidate T-wave is compared to the T-wave template stored for the corresponding estimated "true" heart rate condition. If pathological event detection criteria are met at block 722 based on candidate T-wave signals not matching a corresponding T-wave template when event intervals meet T-wave detection criteria, a pathological event may be detected at block 722 ("yes" branch). A pathological event, e.g., hyperkalemia or hypoglycemia, may be causing increased T-wave amplitude leading to T-wave oversensing, where the T-waves are altered due to the pathological event and therefore do not match the stored T-wave template for the estimated "true" heart rate condition. This situation may preclude detection of an RS-TS morphology pattern at block 712. However, the sensed event interval comparisons made based on the estimated "true" heart rate at block 714 may provide evidence of T-wave oversensing in the presence of a T-wave morphological change due to a pathological event. If pathological event detection criteria are met at block 722, VT/VF detection and therapy may be withheld at block 718.

When an RS-TS pattern is not detected at block 712 and no evidence of R-T and T-R intervals is detected at block 714, or a pathological event is not detected at block 722, the VT/VF detection is not withhold. Control circuit 80 may go on to detect VT/VF when VT/VF detection criteria are satisfied according to an implemented detection algorithm at block 724. A VT/VF therapy may be delivered in response to detecting VT/VF at block 724. In this way, T-wave oversensing in the presence or absence of a confounding pathological event may be detected, and false VT/VF detection and inappropriate therapies may be avoided.

FIG. 9 is a conceptual diagram of a T-wave monitoring programming window 800 that may be generated and displayed by an external programming device, e.g., external device 50 (FIG. 1). Programming window 800 may be displayed by a programming device, which may be located remotely from the patient and the T-wave monitoring medical device. A user may interact with programming window 800 using a touch screen, mouse and pointer, key board, or other user interface for selecting T-wave morphology attributes to be monitored and other control parameters for monitoring T-waves and detecting pathological events.

Programming window 800 is shown in the form of a table including multiple programmable settings for controlling T-wave monitoring. In the first column 802, multiple T-wave attributes are listed which may be programmed to be monitored or not monitored (yes/no, column 804). In other examples, the T-wave attributes selected for monitoring may be selected by clicking on the attribute, selecting from a pull down window, etc. In some examples, all listed attributes may be stored in T-wave templates but may or may not be set as criteria for detecting a pathological event. In other examples, only the attributes programmed to be monitored may be determined and stored in T-wave templates for use in detecting pathological events.

Pathological event detection criteria may be programmable for each selected T-wave attribute as indicated by column 806. In some examples, a percentage change in the value of the T-wave attribute from the stored T-wave template defines a threshold for detecting a change in T-wave morphology that supports a pathological event detection. In other examples, the presence or absence of the attribute, e.g., T-wave inversion, or no change in an attribute may be defined as detection criteria for a given pathological event. For example, a pathological event detection may require a percentage change in one or more T-wave attributes while no change occurs in other attributes.

In column 808, a user may program the time of day that monitoring occurs, which may be specified as one or more times of day, ranges of times of day, or every n hours as examples. In some cases, monitoring may be enabled 24 hours per day. In column 810, the user may select the T-wave template conditions for which detection of changes in the T-wave morphology is enabled. For example, a user may select all sinus or paced heart rates (e.g., excluding non-sinus VT/VF and anti-tachyarrhythmia pacing) or select specific heart rate ranges for which T-wave templates may be generated or T-wave signals are acquired for comparison to the T-wave templates. The user may select specific paced rhythms or all paced rhythms, all or specific patient body postures, all or specific patient physical activity levels, etc. T-wave template conditions may be selected from a list or pull down menu, etc. and categories or ranges of each condition may be selected or enabled as conditions for which T-wave signals will be compared to T-wave templates for detecting a pathological event. In a patient that may experience more than one type of pathological event, multiple programming windows may be opened for programming the T-wave morphology attributes, detection criteria, monitoring times and T-wave template conditions for each type of pathological event to be detected or predicted.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units, circuits or processors associated with, for example, a medical device.

In one or more examples, the functions described may be implemented in hardware, software, firmware, or any combination thereof. If implemented in software or firmware, the functions may be stored as one or more instructions or code on a computer-readable medium and executed by a hardware-based processing unit. Computer-readable media may include non-transitory computer-readable storage media, which corresponds to a tangible medium such as data storage media (e.g., RAM, ROM, EEPROM, flash memory, or any other non-transitory medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

The invention claimed is:

1. A medical device, comprising:
a sensing circuit configured to:
sense a cardiac electrical signal comprising T-waves attendant to ventricular myocardial repolarizations; and
sense ventricular events attendant to ventricular myocardial depolarizations from the cardiac electrical signal according to a plurality of ventricular sensing control parameters; and
a control circuit configured to:
detect a first T-wave template condition;
generate a first T-wave template from at least one T-wave sensed by the sensing circuit during the detected first T-wave template condition;
after generating the first T-wave template, acquire a first T-wave signal from the cardiac electrical signal sensed by the sensing circuit;
compare the acquired first T-wave signal to the first T-wave template;
determine that the first T-wave signal does not match the first T-wave template;
detect a pathological event in response to at least the acquired first T-wave signal not matching the first T-wave template; and
after detecting the pathological event, adjust at least one of the plurality of ventricular sensing control parameters used by the sensing circuit for sensing the ventricular events attendant to ventricular myocardial depolarizations; and
a therapy delivery circuit configured to deliver a therapy to alleviate or prevent the pathological event in response to the control circuit detecting the pathological event.

2. The device of claim 1, wherein the control circuit is further configured to:
identify a plurality of T-wave template conditions including the first T-wave template condition;
for each respective one of the plurality of T-wave template conditions, generate a T-wave template from T-waves of the cardiac electrical signal sensed by the sensing circuit during the respective one of the plurality of T-wave template conditions;
detect a first current T-wave template condition present at a first time that the first T-wave signal is being acquired from the cardiac electrical signal; and
select the first T-wave template from the plurality of generated T-wave templates based on the detected first current T-wave template condition.

3. The device of claim 2, wherein the control circuit is further configured to:
acquire a second T-wave signal from the cardiac electrical signal sensed by the sensing circuit;
detect a second current T-wave template condition present at a second time that the second T-wave signal is being acquired, the second current T-wave template condition being different than the first current T-wave template condition;
select a second T-wave template from among the plurality of generated T-wave templates based on the second current T-wave template condition;
compare the acquired second T-wave signal to the selected second T-wave template; and
detect the pathological event in response to at least one of the first acquired T-wave signal not matching the selected first T-wave template and the second acquired T-wave signal not matching the selected second T-wave template.

4. The device of claim 2, wherein the control circuit is configured to identify each of the plurality of T-wave template conditions by identifying at least one of a heart rate, a paced rhythm condition, an intrinsic atrial rhythm, a patient body posture, a patient activity level, a bioimpedance, a body temperature, and a QRS signal change.

5. The device of claim 2, further comprising a memory having a plurality of bins, each of the plurality of bins configured to store one of the plurality of T-wave templates, a respective T-wave template condition and a status flag;
wherein the control circuit is configured to;
set the status flag to complete in response to the respective T-wave template being generated from a requisite number of T-wave signals acquired during the respective T-wave template condition, and
set the status flag to incomplete in response to less than the requisite number of T-wave signals for generating the T-wave template being acquired during the respective T-wave template condition.

6. The device of claim 2, wherein:
the control circuit is further configured to:
identify the plurality of different T-wave template conditions by identifying a plurality of different heart rates;
detect a ventricular tachyarrhythmia rate of the sensed ventricular events that is greater than a tachyarrhythmia detection rate threshold;
estimate an actual heart rate that is less than the tachyarrhythmia detection rate based on the rate of the sensed ventricular events;
select the first T-wave template from the plurality of T-wave templates based on the estimated actual heart rate; and
withhold a ventricular tachyarrhythmia detection in response to at least the first T-wave signal matching the selected first T-wave template.

7. The device of claim 6, wherein the control circuit is further configured to:
detect T-wave oversensing in response to the first T-wave signal matching the selected first T-wave template; and
in response to detecting the T-wave oversensing, adjust at least one of the plurality of the ventricular sensing control parameters used by the sensing circuit for sensing ventricular events.

8. The device of claim 6, wherein the control circuit is further configured to:
- determine a plurality of sensed ventricular event intervals;
- in response to the first T-wave signal not matching the selected first one of the T-wave templates, establish T-wave detection criteria based on the plurality of sensed ventricular event intervals;
- compare the plurality of sensed ventricular event intervals to the T-wave detection criteria;
- determine that the T-wave detection criteria are met by the plurality of sensed ventricular event intervals; and
- detect the pathological event in response to at least the first T-wave signal not matching the first T-wave template and determining that the T-wave detection criteria are met.

9. The device of claim 1, wherein the control circuit is configured to generate the first T-wave template by:
- adjusting a ventricular sensing control parameter of the plurality of ventricular sensing control parameters used by the sensing circuit for sensing ventricular events;
- acquiring a plurality of T-wave signals sensed from the cardiac electrical signal during the adjusted ventricular sensing control parameter; and
- generating the T-wave template from the acquired plurality of T-wave signals.

10. The device of claim 9, wherein the control circuit is further configured to acquire each of the plurality of T-wave signals by:
- determining a ventricular event interval from the sensed ventricular events attendant to ventricular myocardial depolarizations;
- establishing T-wave detection criteria based on the ventricular event interval;
- identifying three cardiac events sensed consecutively by the sensing circuit during the adjusted ventricular sensing control parameter;
- determining two consecutive event intervals between the three cardiac events;
- comparing the two consecutive event intervals to the T-wave detection criteria;
- determining that the two consecutive event intervals meet the T-wave detection criteria; and
- in response to the two consecutive event intervals meeting the T-wave detection criteria, acquire at least one of the plurality of T-wave signals corresponding to at least one of the three cardiac events.

11. The device of claim 1, further comprising a sensor configured to produce a sensor signal correlated to the pathological event,
- wherein the control circuit is configured to determine that the pathological event is suspected in response to a change in the sensor signal; and
- compare the first T-wave signal to the first T-wave template in response to determining that the pathological event is suspected.

12. The device of claim 1, wherein the control circuit is configured to detect the pathological event by detecting a non-cardiac pathological event in response to the acquired first T-wave signal not matching the T-wave template.

13. The device of claim 1, wherein the control circuit is configured to detect the pathological event by detecting one of: epileptic seizure, hyperglycemia, hypoglycemia, hyperkalemia, hypokalemia, renal failure, hypervolemia, hypovolemia, edema, medication overdosing, medication underdosing, cardiac conduction block, or tachyarrhythmia.

14. A method comprising:
- sensing a cardiac electrical signal comprising T-waves attendant to ventricular myocardial repolarizations;
- sensing ventricular events attendant to ventricular myocardial depolarizations from the cardiac electrical signal according to a plurality of ventricular sensing control parameters;
- detecting a first T-wave template condition;
- generating a first T-wave template from at least one T-wave sensed during the detected first T-wave template condition;
- after generating the first T-wave template, acquiring a first T-wave signal from the sensed cardiac electrical signal;
- comparing the acquired first T-wave signal to the first T-wave template;
- determining that the acquired first T-wave signal does not match the T-wave template;
- detecting a pathological event in response to determining that the acquired first T-wave signal does not match the T-wave template;
- after detecting the pathological event, adjusting at least one of the plurality of ventricular sensing control parameters used for sensing the ventricular events attendant to ventricular myocardial depolarizations; and
- delivering a therapy to alleviate the pathological event in response to detecting the Pathological event.

15. The method of claim 14, further comprising:
- identifying a plurality of T-wave template conditions including the first T-wave template condition;
- for each respective one of the plurality of T-wave template conditions, generating a T-wave template from T-waves sensed from the cardiac electrical signal during the respective one of the plurality of T-wave template conditions;
- detecting a first current T-wave template condition present at a first time that the first T-wave signal is being acquired from the cardiac electrical signal; and
- selecting the first T-wave template from the plurality of generated T-wave templates based on the detected first current T-wave template condition.

16. The method of claim 15, further comprising:
- acquiring a second T-wave signal from the sensed cardiac electrical signal;
- detecting a second current T-wave template condition present at a second time that the second T-wave signal is being acquired, the second current T-wave template condition being different than the first current T-wave template condition;
- selecting a second T-wave template from among the plurality of generated T-wave templates based on the second current T-wave template condition;
- comparing the acquired second T-wave signal to the selected second T-wave template; and
- detecting the pathological event in response to at least one of the first acquired T-wave signal not matching the selected first T-wave template and the second acquired T-wave signal not matching the selected second T-wave template.

17. The method of claim 15, further comprising identifying each of the plurality of T-wave template conditions by identifying at least one of a heart rate, a paced rhythm condition, an intrinsic atrial rhythm, a patient body posture, a patient activity level, a bioimpedance, a body temperature, and a QRS signal change.

18. The method of claim 15, further comprising:
- storing each one of the plurality of T-wave templates with a respective T-wave template condition and status flag;

setting the status flag to complete in response to the respective T-wave template being generated from a requisite number of T-wave signals acquired during the respective T-wave template condition, and setting the status flag to incomplete in response to less than the requisite number of T-wave signals for generating the T-wave template being acquired during the respective T-wave template condition.

19. The method of claim 15, further comprising:

identifying the plurality of different T-wave template conditions by identifying a plurality of different heart rates;

detecting a ventricular tachyarrhythmia rate of the sensed ventricular events that is greater than a tachyarrhythmia detection rate threshold;

estimating an actual heart rate that is less than the tachyarrhythmia detection rate based on the rate of the sensed ventricular events;

selecting the first T-wave template from the plurality of T-wave templates based on the estimated actual heart rate; and withholding a ventricular tachyarrhythmia detection in response to at least the first T-wave signal matching the selected first T-wave template.

20. The method of claim 19, further comprising:

detecting T-wave oversensing in response to the first T-wave signal matching the selected first T-wave template; and in response to detecting the T-wave oversensing, adjusting at least one of the plurality of ventricular sensing control parameters used for sensing the ventricular events.

21. The method of claim 19, further comprising:

determining a plurality of sensed ventricular event intervals;

in response to the first T-wave signal not matching the selected first one of the T-wave templates, comparing the plurality of sensed ventricular event intervals to T-wave detection criteria;

determining that T-wave detection criteria are met by the plurality of sensed ventricular event intervals; and detecting the pathological event in response to at least the first T-wave signal not matching the first T-wave template and determining that the T-wave detection criteria are met.

22. The method of claim 14, wherein generating the first T-wave template comprises:

adjusting a ventricular sensing control parameter of the plurality of ventricular sensing control parameters;

acquiring a plurality of T-wave signals sensed from the cardiac electrical signal during the adjusted ventricular sensing control parameter; and generating the T-wave template from the acquired plurality of T-wave signals.

23. The method of claim 22, wherein acquiring each of the plurality of T-wave signals comprises:

identifying three cardiac events sensed consecutively during the adjusted ventricular sensing control parameter;

determining two consecutive event intervals between the three cardiac events;

comparing the two consecutive event intervals to T-wave detection criteria;

determining that the two consecutive event interval meet the T-wave detection criteria; and in response to the two consecutive event intervals meeting the T-wave detection criteria, acquire at least one of the plurality of T-wave signals corresponding to at least one of the three cardiac events.

24. The method of claim 14, further comprising:

producing a sensor signal correlated to the pathological event, determining that the pathological event is suspected in response to a change in the sensor signal; and comparing the first T-wave signal to the first T-wave template in response to determining that the pathological event is suspected.

25. The method of claim 14, further comprising detecting the pathological event by detecting a non-cardiac pathological event in response to the acquired first T-wave signal not matching the T-wave template.

26. The method of claim 15, wherein detecting the pathological event comprises detecting one of: epileptic seizure, hyperglycemia, hypoglycemia, hyperkalemia, hypokalemia, renal failure, hypervolemia, hypovolemia, edema, medication overdosing, medication under-dosing, cardiac conduction block, or tachyarrhythmia.

27. A non-transitory, computer-readable storage medium comprising a set of instructions which, when executed by a medical device, cause the medical device to:

sense a cardiac electrical signal comprising T-waves attendant to ventricular myocardial repolarizations;

sense ventricular events attendant to ventricular myocardial depolarizations from the cardiac electrical signal according to a plurality of ventricular sensing control parameters;

detect a T-wave template condition;

generate a T-wave template from at least one T-wave sensed from the cardiac electrical signal during the detected T-wave template condition;

after generating the T-wave template, acquire a T-wave signal from the sensed cardiac electrical signal;

compare the acquired T-wave signal to the T-wave template;

determine that the T-wave signal does not match the T-wave template;

detect a pathological event in response to the acquired T-wave signal not matching the T-wave template;

after detecting the pathological event, adjust at least one of the plurality of ventricular sensing control parameters used for sensing ventricular events attendant to ventricular myocardial depolarizations; and deliver a therapy to alleviate the pathological event in response to detecting the Pathological event.

* * * * *